(12) United States Patent
Deb

(10) Patent No.: US 9,186,388 B2
(45) Date of Patent: Nov. 17, 2015

(54) WNT1 FOR TREATMENT OF CARDIOVASCULAR DISORDERS AND INJURIES

(75) Inventor: Arjun Deb, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 13/885,943

(22) PCT Filed: Nov. 17, 2011

(86) PCT No.: PCT/US2011/061138
§ 371 (c)(1),
(2), (4) Date: Aug. 7, 2013

(87) PCT Pub. No.: WO2012/068341
PCT Pub. Date: May 24, 2012

(65) Prior Publication Data
US 2013/0309211 A1    Nov. 21, 2013

Related U.S. Application Data

(60) Provisional application No. 61/414,455, filed on Nov. 17, 2010.

(51) Int. Cl.
| | |
|---|---|
| *A01N 63/00* | (2006.01) |
| *A61K 38/00* | (2006.01) |
| *A61K 48/00* | (2006.01) |
| *C12N 5/02* | (2006.01) |
| *A61K 38/16* | (2006.01) |
| *A61K 31/7088* | (2006.01) |
| *A61K 35/36* | (2015.01) |
| *A61K 35/44* | (2015.01) |
| *C12N 5/00* | (2006.01) |

(52) U.S. Cl.
CPC .............. *A61K 38/00* (2013.01); *A61K 31/7088* (2013.01); *A61K 35/36* (2013.01); *A61K 35/44* (2013.01); *A61K 38/16* (2013.01); *A61K 48/00* (2013.01)

(58) Field of Classification Search
CPC ....... A61K 38/16; A61K 35/44; A61K 35/36; A61K 31/7088
USPC ...................................... 424/93.21; 514/44 R
See application file for complete search history.

(56) References Cited

U.S. PATENT DOCUMENTS

2005/0261189 A1*  11/2005  Larsen et al. .................... 514/12

OTHER PUBLICATIONS

Poelman et al., 2002, Tex Hear Inst J. 29:255-261.*
Carmona et al. "Localization of the Wilm's Tumour Protein WT1 in Avian Embryos". 2001. *Cell Tissue Res.* 303:173.
Cheng et al. "Wnt5a-Mediated Non-Canonical Wnt Signalling Regulates Human Endothelial Cell Proliferation and Migration". 2008. *Biochem. Biophys. Res. Commun.* 365:285.
DasGupta et al. "Multiple Roles for Activated LEF/TCF Transcription Complexes During Hair Follicle Development and Differentiation". 1999. *Development* 126:4557.
Eisenberg et al. "Wnt Signal Transduction and the Formation of the Myocardium". 2006. *Dev. Biol.* 293:305.
Gorden et al. "Wnt Signaling: Multiple Pathways, Multiple Receptors, and Multiple Transcription Factors". 2006. *J. Biol. Chem.* 281:22429.
Gurley et al. "β-Catenin Defines Head Versus Tail Identity During Planarian Regeneration and Homeostasis". 2008. *Science* 319:323.
Kalluri et al. "The Basics of Epithelial-Mesenchymal Transition". 2009. *J. Clin. Invest.* 119:1420.
Kobayashi et al. "Secreted Frizzled Related Protein 2 is a Procollagen C Proteinase Enhancer with a Role in Myocardial Infarction-Associated Fibrosis". 2009. *Nature Cell Biol.* 11:46.
Martinez-Estrada et al. "Wt1 is Required for Cardiovascular Progenitor Cell Formation Through Transcriptional Control of Snail and E-cadherin". 2010. *Nature Genet.* 42:89.
Miratsou et al. "Secreted Frizzled Related Protein 2 (Sfrp2) is the Key Akt-Mesenchymal Stem Cell-Released Paracrine Factor Mediating Myocardial Survival and Repair". 2007. *Proc. Natl. Acad. Sci. USA* 104:1643.
Moore et al. "YAC Complementation Shows a Requirement for Wt1 in the Development Epicardium, Adrenal Gland and Throughout Nephrogenesis". 1999. *Development* 126:1845.
Nusse et al. "Many Tumors Induced by the Mouse Mammary Tumor Virus Contain a Provirus Integrated in the Same Region of the Host Genome". 1982. *Cell* 31:99.
Papkoff et al. "Wnt-1 and HGF Regulate GSK3 Beta Activity and Beta-Catenin Signaling in Mammary Epithelial Cells". 1998. *Biochem. Biophys. Res. Commun.* 247:851.
Petersen et al. "Smed-Betacatenin-1 is Required for Anteroposterior Blastema Polarity in Planarian Regeneration". 2008. *Science.* 319:327.
Thiery et al. "Epithelial-Mesenchymal Transitions in Development and Disease". 2009. *Cell* 139:871.
Vermeulen et al. "Wnt Activity Defines Colon Cancer Stem Cells and is Regulated by the Microenvironment". 2010. *Nature Cell Biol.* 12:468.
Wilm et al. "The Serosal Mesothelium is a Major Source of Smooth Muscle Cells of the Gut Vasculature". 2005. *Development* 132:5317.
You et al. "Inhibition of Wnt-1 Signaling Induces Apoptosis in β-Catenin-Deficient Mesothelioma Cells". 2004. *Cancer Res.* 64:3474.
Zhou et al. "Epicardial Progenitors Contribute to the Cardiomyocyte Lineage in the Developing Heart". 2008. *Nature* 454:109.
Ziemer et al. "Identification of a Mouse Homolog of the Human BTEB2 Transcription Factor as a β-Catenin-Independent Wnt-1-Responsive Gene". 2001. *Mol. Cell. Biol.* 21:562.

* cited by examiner

*Primary Examiner* — Christopher M Babic
*Assistant Examiner* — Kelaginamane T Hiriyanna
(74) *Attorney, Agent, or Firm* — Riverside Law LLP

(57) ABSTRACT

The present invention relates to the discovery of the role of Wnt1 in multiple cardiovascular processes, including cardiac repair, angiogenesis, and stimulation of endothelial progenitor cells. This discovery provides methods of using Wnt1 to treat cardiovascular disorders and injuries.

7 Claims, 18 Drawing Sheets

Figure 3
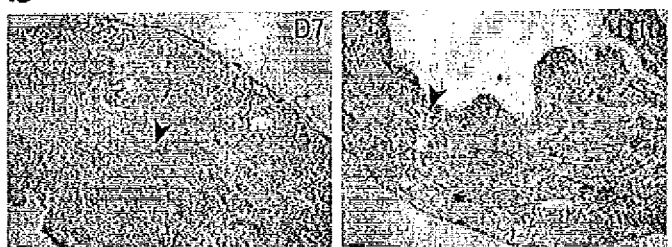
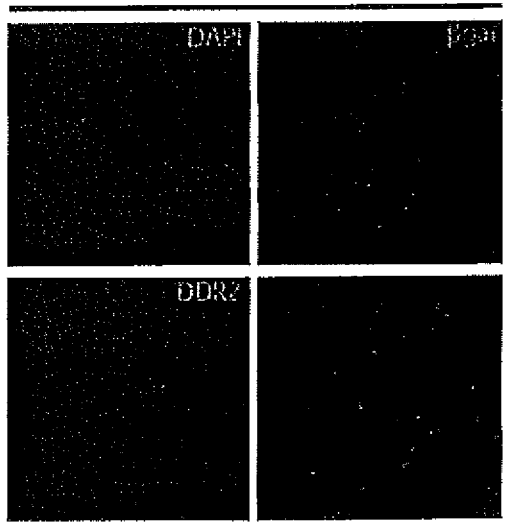
Fibroblasts isolated from sham injured heart
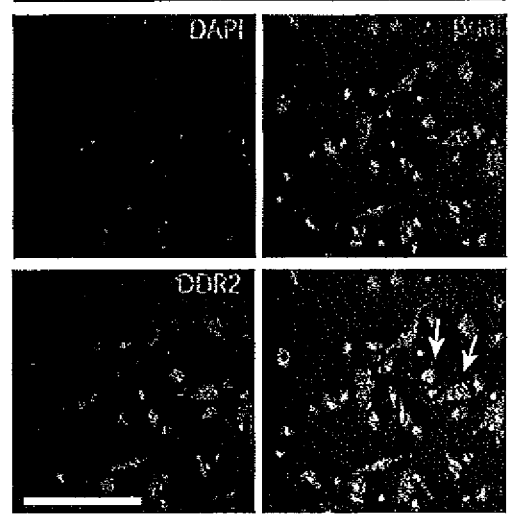
Fibroblasts isolated from injured heart Figure 8
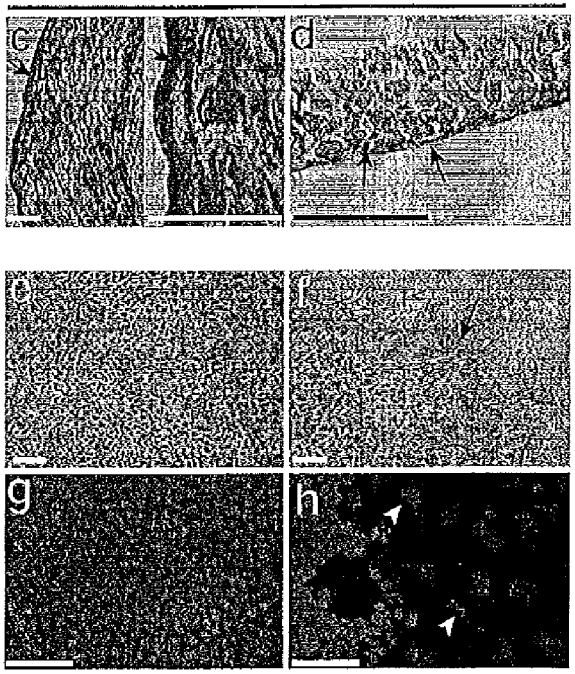
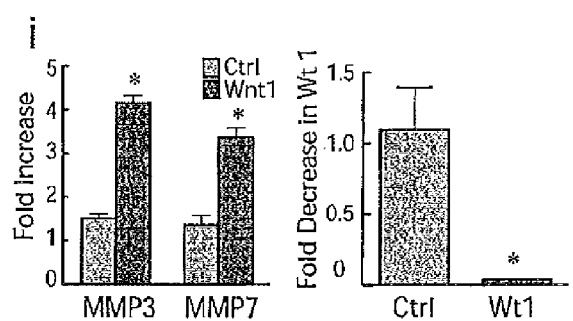
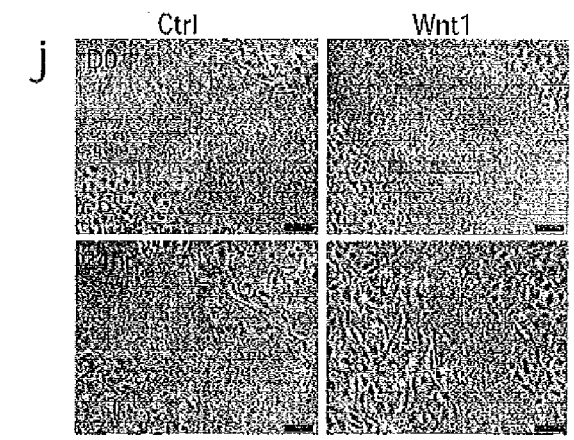
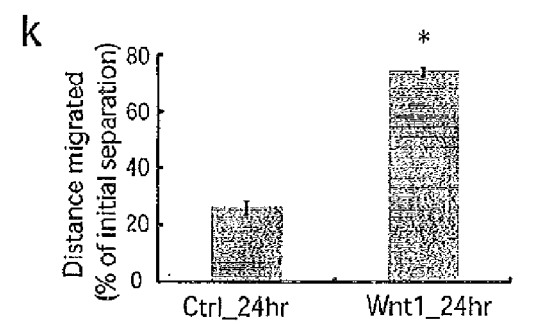
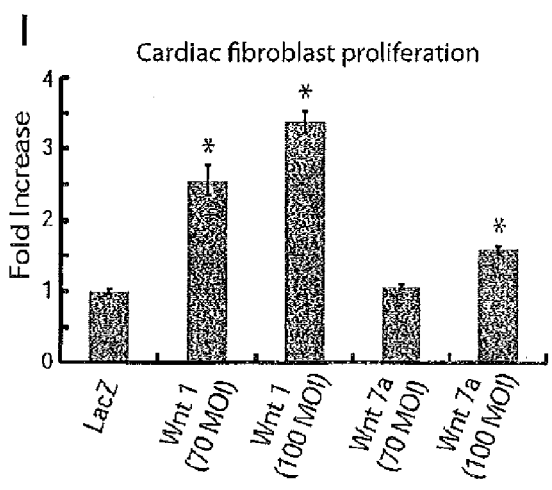

WNT1 FOR TREATMENT OF CARDIOVASCULAR DISORDERS AND INJURIES

STATEMENT OF PRIORITY

This application is a U.S. national phase application filed under 35 U.S.C. §371 claiming benefit to International Patent Application No. PCT/US2011/061138 filed on Nov. 17, 2011, which is entitled to priority under 35 U.S.C. §119(e) to U.S. Provisional Patent Application No. 61/414,455, filed on Nov. 17, 2010, each of which application is hereby incorporated herein by reference in its entirety.

STATEMENT OF FEDERAL SUPPORT

This invention was made with Government support under HL088317, awarded by the National Institutes of Health. The Government has certain rights in the invention.

FIELD OF THE INVENTION

The present invention relates to the discovery of the role played by Wnt1 in multiple cardiovascular processes, including cardiac repair, angiogenesis, and stimulation of endothelial progenitor cells. This discovery provides methods of using Wnt1 to treat cardiovascular disorders and injuries.

BACKGROUND OF THE INVENTION

Heart disease is a leading cause of mortality and morbidity and an emerging public health problem in the developing world (Hunt et al., *J. Am. Cell. Cardiol.* 46:1116 (2005)). Acute injury to the heart commonly occurs following occlusion of a culprit blood vessel with subsequent death of dependent cardiac muscle. The mammalian heart heals by scar formation and the inability of the mammalian heart to regenerate cardiac muscle coupled with a predominantly fibrotic response to acute cardiac injury remains a fundamental biological problem to the therapy of heart disease.

The Wnt signaling system, comprising 19 lipophilic proteins in mammals (Gordon et al., *J. Biol. Chem.* 281:22429 (2006)), plays a critical role in wound repair and regeneration in simple systems such as planaria and hydra (Gurley et al., *Science* 319:323 (2008); Petersen et al., *Science* 319:327 (2008)). Wnts are developmentally important for cardiogenesis (Eisenberg et al., *Dev. Biol.* 293:305 (2006)) and Wnt antagonists exert anti-apoptotic effects on cardiac myocytes as well as affect scarring (Kobayashi et al., *Nature Cell Biol.* 11:46 (2009); Mirotsou et al., *Proc. Natl. Acad. Sci. USA* 104:1643 (2007)); however the precise physiological role of Wnts following acute cardiac injury remains unexplored.

Peripheral vascular disease affects 10-15% of the population in the US above the age of 65 years (Becker et al., *J. Vasc. Interv. Radiol.* 13:7 (2002)), and is a debilitating condition caused by atherosclerotic narrowing and restriction of arterial blood flow to the extremities. Chronic vascular insufficiency induces skin, muscle, and nerve damage and severely reduces functionality of the limbs. New blood vessel formation in the adult has been traditionally thought to arise from proliferation of existing blood vessels (angiogenesis) (Conway et al., *Cardiovasc. Res.* 49:507 (2001)) but a large body of literature suggests that de novo formation of blood vessels from endothelial progenitor cells (vasculogenesis) occurs in post natal life (Asahara et al., *EMBO J.* 18:3964 (1999); Takahashi et al., *Nature Med.* 5:434 (1999); Tepper et al., *Blood* (2004)).

Human endothelial progenitor cells (hEPCs) are known to participate in neovascularization of ischemic tissues (Asahara et al., *EMBO J.* 18:3964 (1999)). Patients with vascular disease have decreased number as well as function of EPCs but molecular strategies to enhance human EPC function remain unclear (Takahashi et al., *Nature Med.* 5:434 (1999)). Genes playing a critical role during development and organogenesis can exert therapeutic effects on postnatal organ dysfunction (Tepper et al., *Blood* (2004); Vasa et al., *Circ. Res.* 89:e1 (2001)). The Wnt signaling system plays a critical role in organogenesis, as well as postnatal processes such as carcinogenesis and wound repair (Nusse et al., *Cell* 31:99 (1982)).

The present invention addresses previous shortcomings in the art by disclosing the role of Wnt1 in both cardiac repair and angiogenesis in ischemic tissue. This discovery provides methods for treating cardiovascular disorders and injuries, including enhancing cardiac repair and increasing blood flow in ischemic tissues.

SUMMARY OF THE INVENTION

The present invention is based, in part, on the discovery of the role of Wnt1 in cardiac repair, angiogenesis, and EPC function. Accordingly, as one aspect, the invention relates to a method of activating the epicardium in the heart of a subject, comprising delivering Wnt1 to the subject.

In another aspect, the invention relates to a method of enhancing the pro-fibrotic function of cardiac fibroblasts in the heart of a subject, comprising delivering Wnt1 to the subject.

In an additional aspect, the invention relates to a method of increasing generation of cardiac fibroblasts in the heart of a subject, comprising delivering Wnt1 to the subject.

In each of these aspects, Wnt1 can be delivered to the subject following cardiac injury or prior to anticipated cardiac injury (e.g., cardiac surgery).

In a further aspect, the invention relates to a method of treating a cardiac disorder or injury in a subject, comprising delivering a therapeutically effective amount of Wnt1 to the subject.

In another aspect, the invention relates to a method of enhancing cardiac repair in a subject, comprising delivering a therapeutically effective amount of Wnt1 to the subject.

In an additional aspect, the invention relates to a method of enhancing cardiac repair in a subject, comprising delivering to the subject a therapeutically effective amount of an agent that stimulates the Wnt/β-catenin pathway.

In a further aspect, the invention relates to a method of increasing the proliferation of EPC, comprising contacting the EPC with Wnt1.

In another aspect, the invention relates to a method of increasing blood vessel formation in an ischemic tissue of a subject, comprising delivering Wnt1 to the ischemic tissue.

In an additional aspect, the invention relates to a method of increasing blood flow in an ischemic tissue of a subject, comprising delivering Wnt1 to the ischemic tissue.

In a further aspect, the invention relates to a method of treating ischemia in a tissue of a subject, comprising delivering Wnt1 to the ischemic tissue.

In another aspect, the invention relates to a method of increasing blood vessel formation in an ischemic tissue of a subject, comprising delivering to the ischemic tissue EPC, wherein the EPC have been contacted with Wnt1 and/or recombinantly express Wnt1.

In an additional aspect, the invention relates to a method of increasing blood flow in an ischemic tissue of a subject, comprising delivering to the ischemic tissue EPC, wherein the EPC have been contacted with Wnt1 and/or recombinantly express Wnt1.

In a further aspect, the invention relates to a method of treating ischemia in a tissue of a subject, comprising delivering to the ischemic tissue EPC, wherein the EPC have been contacted with Wnt1 and/or recombinantly express Wnt1.

In another aspect, the invention relates to an isolated EPC that has been contacted with Wnt1 and/or an isolated EPC that recombinantly expresses Wnt1.

The present invention is explained in greater detail in the drawings herein and the specification set forth below.

BRIEF DESCRIPTION OF THE DRAWINGS

FIGS. 3a-3d show expression of lacZ in uninjured and injured hearts of Wnt1Cre/R26R$^{lacZ}$ mice. (a) Xgal staining of heart in whole mount demonstrates staining in the aortic arch (arrow) and cardiac nerves (arrowheads); (b) Xgal staining of hearts 7 and 10 days post injury shows lacZ cells in region of injury (arrowhead); (c,d) immunostaining of cardiac fibroblasts isolated from (c) sham or (d) injured Wnt1Cre/R26R$^{lacZ}$ animals show cardiac fibroblasts staining for β-galactosidase (arrows) [anti-DDR$^2$ (Santa Cruz Biotechnology), anti-β-galactosidase (MP Biomedicals) antibodies used]. Scale bar: 100 µm.

FIGS. 8a-8l show the epicardium undergoes EMT and generates collagen 1 expressing cardiac fibroblasts after cardiac injury. Xgal staining of hearts of Col1a2Cre(ER)T/R26R$^{lacZ}$ mice following administration of tamoxifen. (a) sham injured heart section (tamoxifen injected only before sham injury) shows rare lacZ expressing cells in the epicardium and myocyte interstitium (arrowhead); (b) day 11 post injury heart section (tamoxifen injected only before injury) shows lacZ positive cells present in subepicardial region (black arrowheads) and absence of epicardial staining (white arrowhead) with only rare epicardial cells expressing lacZ (inset arrow); (c-d) day 11 post injury heart section (tamoxifen injected both before and after injury) shows (c) strong lacZ expression in the epicardium and subepicardial region (arrow); (d) lacZ expressing epicardium adjacent to apparently viable myocytes (arrows); (e-f) epicardial cells treated with (e) BSA or (f) TGFβ shows change in cell shape (arrow); (g-h) Wt-1 staining with anti-Wt1 antibody (DAKO) following (g) BSA or (h) TGFβ treatment [decreased Wt-1 expression in cells undergoing change in shape (arrowhead)]; (i) qPCR of epicardial cells treated with Wnt1 (n=3, *p<0.05; mean±SEM); (j) Effects of Wnt1 on epicardial cell migration in a scratch wound assay; (k) distance migrated by the cells (expressed as % of initial separation, n=3, *p<0.05; mean±SEM); (l) change in cardiac fibroblast proliferation following lentiviral infection of cardiac fibroblasts with either Wnt1, Wnt7A or lacZ gene using a Cyquant assay (n=5, *p<0.05; mean±SEM; MOI-multiplicity of infection). Scale bar: 100 µm.

(j) screening for common angiogenic cytokines shows HGF expression is significantly increased in Wnt1 infected hEPC compared to GFP infected hEPC (n=3, *p<005) (vWF=von Willebrand factor, eNOS=endothelial nitric oxide synthase, FGF=fibroblast growth factor, VEGF=vascular endothelial growth factor, IGF=insulin-like growth factor, MMP=matrix metalloproteinase, PECAM=platelet/endothelial cell adhesion molecule, VECAD=vascular endothelial cadherin); (b-e, bar: 100 µm); (f-i, bar: 50 µm).

Figure 18:
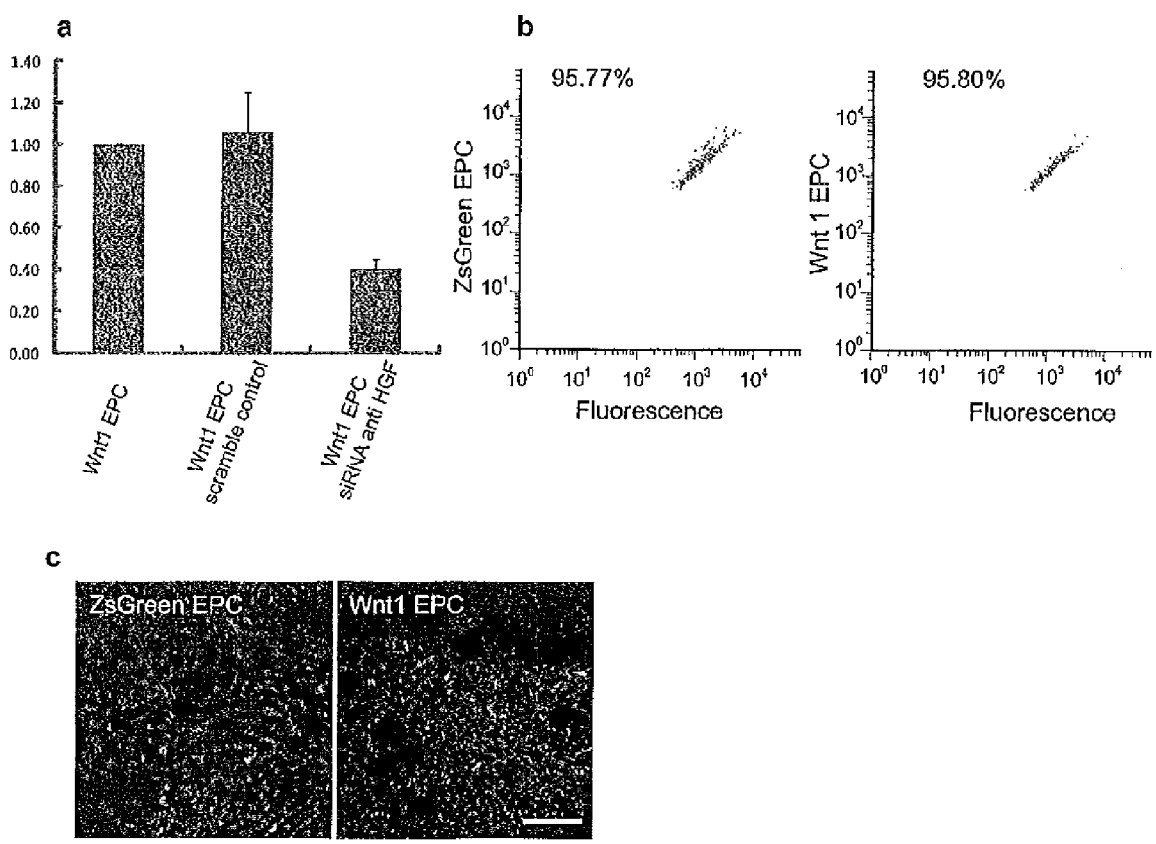

FIGS. 18a-18c. (a) QPCR for HGF expression in Wnt1 overexpressing hEPCs, Wnt1 overexpressing hEPCs treated with scrambled siRNA control and Wnt1 overexpressing hEPCs treated with siRNA directed against HGF; (b) following WPC infection with ZsGreen or Wnt1, hEPCs were sorted by flow cytometry. Post sorting analysis showed the purity of cell populations used in our experiments was >95%; (c) seven days following hEPC injection, cells survive in similar numbers in ZsGreen-hEPCs and Wnt1-hEPCs, but do not colocalize with isolectin (dark gray); (c, bar: 125 µm).

DETAILED DESCRIPTION OF THE INVENTION

The present invention will now be described in more detail with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, patent publications and other references cited herein are incorporated by reference in their entireties for the teachings relevant to the sentence and/or paragraph in which the reference is presented.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. §1,822 and established usage.

Except as otherwise indicated, standard methods known to those skilled in the art may be used for cloning genes, amplifying and detecting nucleic acids, and the like. Such techniques are known to those skilled in the art. See, e.g., Sambrook et al., Molecular Cloning; A Laboratory Manual 2nd Ed. (Cold Spring Harbor, N.Y., 1989); Ausubel et al. Current Protocols in Molecular Biology (Green Publishing Associates, Inc. and John Wiley & Sons, Inc., New York).

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate, if the specification states that a complex comprises components A, B and C, it is specifically intended that any of A, B or C, or a combination thereof, can be omitted and disclaimed singularly or in any combination.

I. Definitions

As used in the description of the invention and the appended claims, the singular forms "a," "an," and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of polypeptide, dose, time, temperature, enzymatic activity or other biological activity and the like, is meant to encompass variations of ±20%, ±10%, ±5%, ±1%, ±0.5%, or even ±0.1% of the specified amount.

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising."

The terms "enhance" or "stimulate" or "activate," as used herein, refers to an increase in at least one biological activity of a protein of interest of the invention, e.g., an increase of at least about 10%, 20%, 30%, 40%, 50%, 60%, 70%, 80%, 90%, 100%, or more.

The terms "decrease" or "reduce" or "inhibit" or "inactivate," as used herein, refers to a decrease in at least one biological activity of a protein of interest of the invention, e.g., a decrease of at least about 10%, 20%, 30%, 40%, 50%, 60%, 70%, 80%, 90%, or 100%.

A "therapeutically effective" amount as used herein is an amount that provides some improvement or benefit to the subject. Alternatively stated, a "therapeutically effective" amount is an amount that will provide some alleviation, mitigation, or decrease in at least one clinical symptom in the subject. Those skilled in the art will appreciate that the therapeutic effects need not be complete or curative, as long as some benefit is provided to the subject.

By the terms "treat," "treating," or "treatment," it is intended that the severity of the subject's condition is reduced or at least partially improved or modified and that some alleviation, mitigation or decrease in at least one clinical symptom is achieved.

"Prevent" or "preventing" or "prevention" refer to prevention or delay of the onset of the disorder and/or a decrease in the severity of the disorder in a subject relative to the severity that would develop in the absence of the methods of the invention. The prevention can be complete, e.g., the total absence of ischemia in a subject. The prevention can also be partial, such that the occurrence of ischemia in a subject is less than that which would have occurred without the present invention.

As used herein, "nucleic acid," "nucleotide sequence," and "polynucleotide" are used interchangeably and encompass both RNA and DNA, including cDNA, genomic DNA, mRNA, synthetic (e.g., chemically synthesized) DNA or RNA and chimeras of RNA and DNA. The term polynucleotide or nucleotide sequence refers to a chain of nucleotides without regard to length of the chain. The nucleic acid can be double-stranded or single-stranded. Where single-stranded, the nucleic acid can be a sense strand or an antisense strand.

The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. The present invention further provides a nucleic acid that is the complement (which can be either a full complement or a partial complement) of a nucleic acid or nucleotide sequence of this invention.

An "isolated polynucleotide" is a nucleotide sequence (e.g., DNA and/or RNA) that is not immediately contiguous with nucleotide sequences with which it is immediately contiguous (one on the 5' end and one on the 3' end) in the naturally occurring genome of the organism from which it is derived. Thus, in one embodiment, an isolated polynucleotide includes some or all of the 5' non-coding (e.g., promoter) sequences that are immediately contiguous to a coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant DNA that is part of a hybrid nucleic acid encoding an additional polypeptide or peptide sequence. An isolated polynucleotide that includes a gene is not a fragment of a chromosome that includes such gene, but rather includes the coding region and regulatory regions associated with the gene, but no additional genes naturally found on the chromosome.

The term "isolated" also can refer to a nucleic acid, nucleotide sequence or polypeptide that is substantially free of cellular material, viral material, and/or culture medium (when produced by recombinant DNA techniques), or chemical precursors or other chemicals (when chemically synthesized). Moreover, an "isolated fragment" is a fragment of a nucleic acid, nucleotide sequence or polypeptide that is not naturally occurring as a fragment and would not be found in the natural state. "Isolated" does not mean that the preparation is technically pure (homogeneous), but it is sufficiently pure to provide the polypeptide or nucleic acid in a form in which it can be used for the intended purpose.

An "isolated" cell refers to a cell that is separated from other components with which it is normally associated in its natural state. For example, an isolated cell can be a cell in culture medium and/or a cell in a pharmaceutically acceptable carrier of this invention. Thus, an isolated cell can be delivered to and/or introduced into a subject. In some embodiments, an isolated cell can be a cell that is removed from a subject and manipulated as described herein ex vivo and then returned to the subject.

The term "fragment," as applied to a nucleic acid, nucleotide sequence, or polynucleotide, will be understood to mean a nucleotide sequence of reduced length relative to a reference nucleic acid and comprising, consisting essentially of, and/or consisting of a nucleotide sequence of contiguous nucleotides identical or almost identical (e.g., 90%, 92%, 95%, 98%, 99% identical) to the reference nucleic acid. Such a nucleic acid fragment according to the invention may be, where appropriate, included in a larger polynucleotide of which it is a constituent. In some embodiments, such fragments can comprise, consist essentially of, and/or consist of oligonucleotides having a length of at least about 8, 10, 12, 15, 20, 25, 30, 35, 40, 45, 50, 75, 100, 150, 200, or more consecutive nucleotides of a nucleic acid according to the invention. In other embodiments, such fragments can comprise, consist essentially of, and/or consist of oligonucleotides having a length of less than about 200, 150, 100, 75, 50, 45, 40, 35, 30, 25, 20, 15, 12, 10, 8, or less consecutive nucleotides of a nucleic acid according to the invention.

The term "fragment," as applied to a polypeptide, will be understood to mean an amino acid sequence of reduced length relative to a reference polypeptide and comprising, consisting essentially of, and/or consisting of an amino acid sequence of contiguous amino acids identical or almost identical (e.g., 90%, 92%, 95%, 98%, 99% identical) to the reference polypeptide. Such a polypeptide fragment according to the invention may be, where appropriate, included in a larger polypeptide of which it is a constituent. In some embodiments, such fragments can comprise, consist essentially of, and/or consist of peptides having a length of at least about 4, 6, 8, 10, 12, 15, 20, 25, 30, 35, 40, 45, 50, 75, 100, 150, 200, or more consecutive amino acids of a polypeptide according to the invention. In other embodiments, such fragments can comprise, consist essentially of, and/or consist of peptides having a length of less than about 200, 150, 100, 75, 50, 45, 40, 35, 30, 25, 20, 15, 12, 10, 8, or less consecutive amino acids of a polypeptide according to the invention.

A "vector" is any nucleic acid molecule for the cloning of and/or transfer of a nucleic acid into a cell. A vector may be a replicon to which another nucleotide sequence may be attached to allow for replication of the attached nucleotide sequence. A "replicon" can be any genetic element (e.g., plasmid, phage, cosmid, chromosome, viral genome) that functions as an autonomous unit of nucleic acid replication in vivo, i.e., capable of replication under its own control. The term "vector" includes both viral and nonviral (e.g., plasmid) nucleic acid molecules for introducing a nucleic acid into a cell in vitro, ex vivo, and/or in vivo. A large number of vectors known in the art may be used to manipulate nucleic acids, incorporate response elements and promoters into genes, etc. For example, the insertion of the nucleic acid fragments corresponding to response elements and promoters into a suitable vector can be accomplished by ligating the appropriate nucleic acid fragments into a chosen vector that has complementary cohesive termini. Alternatively, the ends of the nucleic acid molecules may be enzymatically modified or any site may be produced by ligating nucleotide sequences (linkers) to the nucleic acid termini. Such vectors may be engineered to contain sequences encoding selectable markers that provide for the selection of cells that contain the vector and/or have incorporated the nucleic acid of the vector into the cellular genome. Such markers allow identification and/or selection of host cells that incorporate and express the proteins encoded by the marker. A "recombinant" vector refers to a viral or non-viral vector that comprises one or more heterologous nucleotide sequences (i.e., transgenes), e.g., two, three, four, five or more heterologous nucleotide sequences.

Viral vectors have been used in a wide variety of gene delivery applications in cells, as well as living animal subjects. Viral vectors that can be used include, but are not limited to, retrovirus, lentivirus, adeno-associated virus, poxvirus, alphavirus, baculovirus, vaccinia virus, herpes virus, Epstein-Barr virus, adenovirus, geminivirus, and caulimovirus vectors. Non-viral vectors include plasmids, liposomes, electrically charged lipids (cytofectins), nucleic acid-protein complexes, and biopolymers. In addition to a nucleic acid of interest, a vector may also comprise one or more regulatory regions, expression control sequences, and/or selectable markers useful in selecting, measuring, and monitoring nucleic acid transfer results (e.g., delivery to specific tissues, duration of expression, etc.).

Vectors may be introduced into the desired cells by methods known in the art, e.g., transfection, electroporation, microinjection, transduction, cell fusion, DEAE dextran, calcium phosphate precipitation, lipofection (lysosome fusion), use of a gene gun, or a nucleic acid vector transporter (see, e.g., Wu et al., *J. Biol. Chem.* 267:963 (1992); Wu et al., *J. Biol. Chem.* 263:14621 (1988); and Hartmut et al., Canadian Patent Application No. 2,012,311, filed Mar. 15, 1990).

In some embodiments, a polynucleotide of this invention can be delivered to a cell in vivo by lipofection. Synthetic cationic lipids designed to limit the difficulties and dangers encountered with liposome-mediated transfection can be used to prepare liposomes for in vivo transfection of a nucleotide sequence of this invention (Feigner et al., *Proc. Natl. Acad. Sci. USA* 84:7413 (1987); Mackey, et al., *Proc. Natl. Acad. Sci. U.S.A.* 85:8027 (1988); and Ulmer et al., *Science* 259:1745 (1993)). The use of cationic lipids may promote encapsulation of negatively charged nucleic acids, and also promote fusion with negatively charged cell membranes (Feigner et al., *Science* 337:387 (1989)). Particularly useful lipid compounds and compositions for transfer of nucleic acids are described in International Patent Publications WO95/18863 and WO96/17823, and in U.S. Pat. No. 5,459,127. The use of lipofection to introduce exogenous nucleotide sequences into specific organs in vivo has certain practical advantages. Molecular targeting of liposomes to specific cells represents one area of benefit. In representative embodiments, transfection is directed to particular cell types in a tissue with cellular heterogeneity, such as pancreas, liver, kidney, and the brain. Lipids may be chemically coupled to other molecules for the purpose of targeting (Mackey, et al., 1988, supra). Targeted peptides, e.g., hormones or neurotransmitters, and proteins such as antibodies, or non-peptide molecules can be coupled to liposomes chemically.

In various embodiments, other molecules can be used for facilitating delivery of a nucleic acid in vivo, such as a cationic oligopeptide (e.g., WO95/21931), peptides derived from nucleic acid binding proteins (e.g., WO96/25508), and/or a cationic polymer (e.g., WO95/21931).

It is also possible to introduce a vector in vivo as naked nucleic acid (see U.S. Pat. Nos. 5,693,622, 5,589,466 and 5,580,859). Receptor-mediated nucleic acid delivery approaches can also be used (Curie et al., *Hum. Gene Ther.* 3:147 (1992); Wu et al., *J. Biol. Chem.* 262:4429 (1987)).

The term "transfection" or "transduction" means the uptake of exogenous or heterologous nucleic acid (RNA and/or DNA) by a cell. A cell has been "transfected" or "transduced" with an exogenous or heterologous nucleic acid when such nucleic acid has been introduced or delivered inside the cell. A cell has been "transformed" by exogenous or heterologous nucleic acid when the transfected or transduced nucleic acid imparts a phenotypic change in the cell and/or a change in an activity or function of the cell. The transforming nucleic acid can be integrated (covalently linked) into chromosomal DNA making up the genome of the cell or it can be present as a stable plasmid.

As used herein, the terms "protein" and "polypeptide" are used interchangeably and encompass peptides, unless indicated otherwise. In some embodiments, a peptide is a chain of amino acids having a length of about 3 to about 50 residues.

A "fusion protein" is a polypeptide produced when two heterologous nucleotide sequences or fragments thereof coding for two (or more) different polypeptides and/or peptides not found fused together in nature are fused together in the correct translational reading frame. In one embodiment, fusion polypeptides include fusions of a polypeptide of the invention (or a fragment thereof) to a polypeptide that is useful for identifying and/or purifying the fusion protein, e.g., all or a portion of glutathione-S-transferase, maltose-binding protein, or a reporter protein (e.g., Green Fluorescent Protein, β-glucuronidase, β-galactosidase, luciferase, etc.), hemagglutinin, c-myc, FLAG epitope, etc.

As used herein, a "functional" polypeptide or "functional fragment" is one that substantially retains at least one biological activity normally associated with that polypeptide (e.g., catalytic activity, ligand binding). In particular embodiments, the "functional" polypeptide or "functional fragment" substantially retains all of the activities possessed by the unmodified peptide. By "substantially retains" biological activity, it is meant that the polypeptide retains at least about 20%, 30%, 40%, 50%, 60%, 75%, 85%, 90%, 95%, 97%, 98%, 99%, or more, of the biological activity of the native polypeptide (and can even have a higher level of activity than the native polypeptide). A "non-functional" polypeptide is one that exhibits little or essentially no detectable biological activity normally associated with the polypeptide (e.g., at most, only an insignificant amount, e.g., less than about 10% or even 5%). Biological activities such as protein binding and catalysis can be measured using assays that are well known in the art and as described herein.

By the term "express" or "expression" of a polynucleotide coding sequence, it is meant that the sequence is transcribed, and optionally, translated. Typically, according to the present invention, expression of a coding sequence of the invention will result in production of the polypeptide of the invention. The entire expressed polypeptide or fragment can also function in intact cells without purification.

As used herein, the term "activating the epicardium" refers to stimulation of the epicardium to undergo epicardial cell expansion and/or produce cardiac fibroblasts.

As used herein, the term "enhancing the pro-fibrotic function" refers to stimulating cardiac fibroblasts to produce fibrotic tissue and ultimately cardiac repair.

As used herein, the term "enhancing cardiac repair" refers to increasing the amount of repair and/or decreasing the time required to complete repair of the heart.

As used herein, the term "Wnt1/β-catenin pathway" refers to the signaling pathway mediated by Wnt1 and β-catenin and any agent upstream or downstream of Wnt1 and β-catenin in the pathway.

As used herein, the term "functional properties" with respect to EPC refers to the ability of EPC to promote angiogenesis and/or vasculogenesis.

II. Methods of Enhancing Cardiac Repair

The present invention is based, in part, on the discovery of the role of Wnt1 in activation of the epicardium, production of cardiac fibroblasts, and cardiac repair. Stimulation of the Wnt1/β-catenin increases activation of the epicardium, which leads to enhanced cardiac repair and may lead to cardiac regeneration. Thus, one aspect of the invention relates to a method of activating the epicardium in the heart of a subject, comprising delivering Wnt1 to the subject.

In another aspect, the invention relates to a method of enhancing the pro-fibrotic function of cardiac fibroblasts in the heart of a subject, comprising delivering Wnt1 to the subject.

In an additional aspect, the invention relates to a method of increasing generation of cardiac fibroblasts in the heart of a subject, comprising delivering Wnt1 to the subject.

In a further aspect, the invention relates to a method of treating a cardiac disorder or injury in a subject, comprising delivering a therapeutically effective amount of Wnt1 to the subject.

In another aspect, the invention relates to a method of enhancing cardiac repair in a subject, comprising delivering a therapeutically effective amount of Wnt1 to the subject.

In each of these methods, the subject can be one that is in need of cardiac repair, e.g., one that currently has or has previously had a cardiac disorder or cardiac injury. The disorder or injury can be due to, e.g., cardiac ischemia, myocardial infarction, trauma, atherosclerosis, or any other cause. In certain embodiments, the subject can be one that is at risk for a cardiac disorder or injury (e.g., a subject who will be undergoing heart surgery or is exhibiting signs of cardiac weakening) and the method is carried out to prevent and/or delay further damage to the heart.

In certain embodiments, the Wnt1 is delivered directly to the heart of the subject. For example, the Wnt1 can be injected into the heart, e.g., into the epicardium or into the area of injury. In other embodiments, the Wnt1 can be delivered locally, e.g., into blood vessels leading into the heart. In further embodiments, the Wnt1 can be delivered systemically, e.g., intravenously.

The delivery of Wnt1 to a subject can be carried out by any means known in the art. In one embodiment, delivering Wnt1 comprises delivering a Wnt1 polypeptide or a functional fragment or homolog thereof. In another embodiment, delivering Wnt1 comprises delivering a polynucleotide encoding a Wnt1 polypeptide or a functional fragment or homolog thereof. In a further embodiment, delivering Wnt1 comprises delivering a cell expressing a Wnt1 polypeptide or a functional fragment or homolog thereof, e.g., a cell that has been modified to recombinantly express Wnt1 or a functional fragment or homolog thereof.

In certain embodiments, the Wnt1 protein is a mammalian Wnt1 protein, e.g., a human Wnt1 protein. In some embodiments, the Wnt1 polypeptide comprises, consists essentially of, or consists of an amino acid sequence that is at least 70% identical, e.g., at least 75%, 80%, 85%, 90%, 95%, 96%, 97%, 98%, or 99% identical to the publicly known amino acid sequence or a functional fragment thereof. Amino acid and nucleotide sequences of Wnt1 are well known in the art and are available in databases such as GenBank. Exemplary sequences include the human Wnt1 sequence (Accession No. NM_005430), mouse Wnt1 sequence (Accession No. NM_021279), and rat Wnt1 sequence (Accession No. NM_001105714), each herein incorporated by reference. The Wnt1 polypeptide also includes functional portions or fragments. The length of the fragment is not critical as long as it substantially retains the biological activity of Wnt1 (e.g., angiogenic activity). Illustrative fragments comprise at least about 4, 6, 8, 10, 12, 15, 20, 25, 30, 35, 40, 45, 50, 75, 100, 150, 200, or more contiguous amino acids of Wnt1.

As used herein, the term "homolog" is used to refer to a polypeptide which differs from a naturally occurring polypeptide by minor modifications to the naturally occurring polypeptide, but which substantially retains a biological activity of the naturally occurring polypeptide. Minor modifications include, without limitation, changes in one or a few amino acid side chains, changes to one or a few amino acids (including deletions, insertions, and substitutions), e.g., 1, 2, 3, 4, 5, 6, 7, 8, 9, or 10 amino acids, changes in stereochemistry of one or a few atoms, and minor derivatizations, including, without limitation, methylation, glycosylation, phosphorylation, acetylation, myristoylation, prenylation, palmitation, amidation, and addition of glycosylphosphatidyl inositol. The term "substantially retains," as used herein, refers to a fragment, homolog, or other variant of a polypeptide that retains at least about 20% of the activity of the naturally occurring polypeptide (e.g., angiogenic activity), e.g., about 30%, 40%, 50% or more. Angiogenic activity can be measured by, e.g., measuring cell proliferation, angiogenic sprouting, tubule formation, or migration and invasion ability. Other biological activities may include receptor binding, ligand binding, induction of a growth factor, a cell signal transduction event, etc.

Likewise, those skilled in the art will appreciate that the present invention also encompasses fusion polypeptides comprising Wnt1 (or a functional fragment thereof). For example, it may be useful to express Wnt1 as a fusion protein that can be recognized by a commercially available antibody (e.g., FLAG motifs) or as a fusion protein that can otherwise be more easily purified (e.g., by addition of a poly-His tail). Additionally, fusion proteins that enhance the stability of Wnt1 may be produced, e.g., fusion proteins comprising maltose binding protein (MBP) or glutathione-S-transferase. As another alternative, the fusion protein can comprise a reporter molecule. In other embodiments, the fusion protein can comprise a polypeptide that provides a function or activity that is the same as or different from the activity of Wnt1, e.g., a targeting, binding, or enzymatic activity or function.

Likewise, it will be understood that the Wnt1 polypeptides specifically disclosed herein will typically tolerate substitutions in the amino acid sequence and substantially retain biological activity. Amino acid substitutions may be based on any characteristic known in the art, including the relative similarity or differences of the amino acid side-chain substituents, for example, their hydrophobicity, hydrophilicity, charge, size, and the like.

Amino acid substitutions other than those disclosed herein may be achieved by changing the codons of the DNA sequence (or RNA sequence), according to the following codon table:

TABLE 1

| Amino Acid | | | Codons |
| --- | --- | --- | --- |
| Alanine | Ala | A | GCA GCC GCG GCT |
| Cysteine | Cys | C | TGC TGT |
| Aspartic acid | Asp | D | GAC GAT |
| Glutamic acid | Glu | E | GAA GAG |
| Phenylalanine | Phe | F | TTC TTT |
| Glycine | Gly | G | GGA GGC GGG GGT |
| Histidine | His | H | CAC CAT |
| Isoleucine | Ile | I | ATA ATC ATT |
| Lysine | Lys | K | AAA AAG |
| Leucine | Leu | L | TTA TTG CTA CTC CTG CTT |
| Methionine | Met | M | ATG |
| Asparagine | Asn | N | AAC AAT |
| Proline | Pro | P | CCA CCC CCG CCT |
| Glutamine | Gln | Q | CAA CAG |
| Arginine | Arg | R | AGA AGG CGA CGC CGG CGT |
| Serine | Ser | S | AGC ACT TCA TCC TCG TCT |
| Threonine | Thr | T | ACA ACC ACG ACT |

TABLE 1-continued

| Amino Acid | | | Codons |
|---|---|---|---|
| Valine | Val | V | GTA GTC GTG GTT |
| Tryptophan | Trp | W | TGG |
| Tyrosine | Tyr | Y | TAC TAT |

In identifying amino acid sequences encoding Wnt1 polypeptides other than those specifically disclosed herein, the hydropathic index of amino acids may be considered. The importance of the hydropathic amino acid index in conferring interactive biologic function on a protein is generally understood in the art (see, Kyte and Doolittle, *J. Mol. Biol.* 157:105 (1982); incorporated herein by reference in its entirety). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle, id.), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

Accordingly, the hydropathic index of the amino acid (or amino acid sequence) may be considered when modifying the polypeptides specifically disclosed herein.

It is also understood in the art that the substitution of amino acids can be made on the basis of hydrophilicity. U.S. Pat. No. 4,554,101 (incorporated herein by reference in its entirety) states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (±3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Thus, the hydrophilicity of the amino acid (or amino acid sequence) may be considered when identifying additional polypeptides beyond those specifically disclosed herein.

In embodiments of the invention, the polynucleotide encoding the Wnt1 polypeptide (or functional fragment) will hybridize to the nucleic acid sequences specifically disclosed herein or fragments thereof under standard conditions as known by those skilled in the art and encode a functional polypeptide or functional fragment thereof.

For example, hybridization of such sequences may be carried out under conditions of reduced stringency, medium stringency or even stringent conditions (e.g., conditions represented by a wash stringency of 35-40% formamide with 5×Denhardt's solution, 0.5% SDS and 1×SSPE at 37° C.; conditions represented by a wash stringency of 40-45% formamide with 5×Denhardt's solution, 0.5% SDS and 1×SSPE at 42° C.; and conditions represented by a wash stringency of 50% formamide with 5×Denhardt's solution, 0.5% SDS and 1×SSPE at 42° C., respectively) to the polynucleotide sequences encoding the Wnt1 polypeptide or functional fragments thereof specifically disclosed herein. See, e.g., Sambrook et al., Molecular Cloning: A Laboratory Manual 2nd Ed. (Cold Spring Harbor, N.Y., 1989).

In other embodiments, polynucleotide sequences encoding the Wnt1 polypeptide have at least about 70%, 80%, 85%, 90%, 95%, 96%, 97%, 98%, 99% or higher sequence identity with the publicly known nucleic acid sequences (disclosed in the GenBank accession numbers listed above) or functional fragments thereof and encode a functional polypeptide or functional fragment thereof.

Further, it will be appreciated by those skilled in the art that there can be variability in the polynucleotides that encode Wnt1 (and fragments thereof) due to the degeneracy of the genetic code. The degeneracy of the genetic code, which allows different nucleic acid sequences to code for the same polypeptide, is well known in the literature (See, e.g., Table 1).

Likewise, the Wnt1 polypeptide (and fragments thereof) includes polypeptides that have at least about 70%, 80%, 85%, 90%, 95%, 96%, 97%, 98%, 99% or higher amino acid sequence identity with the publicly known polypeptide sequences.

As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, *Adv. Appl. Math,* 2:482 (1981), by the sequence identity alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351 (1987); the method is similar to that described by Higgins & Sharp, *CABIOS* 5:151 (1989).

Another example of a useful algorithm is the BLAST algorithm, described in Altschul et al., *J. Mol. Biol.* 215:403 (1990) and Karlin et al., *Proc. Natl. Acad. Sci. USA* 90:5873 (1993). A particularly useful BLAST program is the WU-BLAST-2 program which was obtained from Altschul et al., *Meth. Enzymol.,* 266:460 (1996); blast.wustl/edu/blast/README.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., *Nucleic Acids Res.* 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity with respect to the coding sequence of the polypeptides disclosed herein is defined as the percentage of nucleotide residues in the candidate sequence that are identical with the nucleotides in the polynucleotide specifically disclosed herein.

The alignment may include the introduction of gaps in the sequences to be aligned. In addition, for sequences which contain either more or fewer amino acids than the polypeptides specifically disclosed herein, it is understood that in one embodiment, the percentage of sequence identity will be determined based on the number of identical amino acids in relation to the total number of amino acids. Thus, for example, sequence identity of sequences shorter than a sequence specifically disclosed herein, will be determined using the number of amino acids in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

Polypeptides and fragments of Wnt1 can be modified for in vivo use by the addition, at the amino- and/or carboxyl-terminal ends, of a blocking agent to facilitate survival of the polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill. Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Likewise, the peptides can be covalently or noncovalently coupled to pharmaceutically acceptable "carrier" proteins prior to administration.

Another embodiment of the invention relates to homologs of the Wnt1 polypeptide that are peptidomimetic compounds that are designed based upon the amino acid sequences of the functional polypeptide fragments. Peptidomimetic compounds are synthetic compounds having a three-dimensional conformation (i.e., a "peptide motif") that is substantially the same as the three-dimensional conformation of a selected peptide. The peptide motif provides the peptidomimetic compound with the ability to enhance angiogenesis in a manner qualitatively identical to that of the functional fragment from which the peptidomimetic was derived. Peptidomimetic compounds can have additional characteristics that enhance their therapeutic utility, such as increased cell permeability and prolonged biological half-life.

The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbon A, dimethylene and ketomethylene bonds, are known in the art to be generally useful substitutes for peptide bonds in the construction of protease-resistant peptidomimetics.

In some embodiments of the invention, Wnt1 is delivered to a subject by delivering a cell expressing a Wnt1 polypeptide or a functional fragment or homolog thereof. The cell can be one that does or does not naturally express Wnt1. In either embodiment, the cell can be modified to recombinantly express Wnt1 or a fragment or homolog thereof. The recombinantly expressed Wnt1 can be the same as or different from the Wnt1 naturally expressed by the cell. The cell to be modified can be a primary cell isolated from a subject, a cultured cell, or a cell from a cell line. In one embodiment, the cell is isolated from a subject, modified to express Wnt1 and then returned to the same subject or a different subject. In another embodiment, the modified cell is cultured to increase the number of cells prior to delivering the cell to a subject.

In certain embodiments, the Wnt1 polynucleotides, polypeptides or homologs thereof, or cells expressing Wnt1 are administered directly to the subject. Generally, the products of the invention will be suspended in a pharmaceutically-acceptable carrier (e.g., physiological saline) and administered orally or by intravenous infusion, or injected subcutaneously, intramuscularly, intrathecally, intraperitoneally, intrarectally, intravaginally, intranasally, intragastrically, intratracheally, or intrapulmonarily. In certain embodiments the products are delivered directly to the site of the disease or disorder, such as the heart or ischemic tissue. The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01-100.0 µg/kg. Wide variations in the needed dosage are to be expected in view of the variety of polypeptides and fragments available and the differing efficiencies of various routes of administration. For example, oral administration would be expected to require higher dosages than administration by i.v. injection. Variations in these dosage levels can be adjusted using standard empirical routines for optimization as is well understood in the art. Encapsulation of the polypeptide, polynucleotide, or cell in a suitable delivery vehicle (e.g., polymeric microparticles or implantable devices) may increase the efficiency of delivery, particularly for oral delivery.

According to certain embodiments, the polypeptides, polynucleotides, or cells can be targeted to specific cells or tissues in vivo. Targeting delivery vehicles, including liposomes and viral vector systems are known in the art. For example, a liposome can be directed to a particular target cell or tissue by using a targeting agent, such as an antibody, soluble receptor or ligand, incorporated with the liposome, to target a particular cell or tissue to which the targeting molecule can bind. Targeting liposomes are described, for example, in Ho et al., *Biochemistry* 25:5500 (1986); Ho et al. *J. Biol. Chem.* 262: 13979 (1987); Ho et al., *J. Biol. Chem.* 262:13973 (1987); and U.S. Pat. No. 4,957,735 to Huang et al., each of which is incorporated herein by reference in its entirety). Enveloped viral vectors can be modified to deliver a nucleic acid molecule to a target cell by modifying or substituting an envelope protein such that the virus infects a specific cell type. In adenoviral vectors, the gene encoding the attachment fibers can be modified to encode a protein domain that binds to a cell-specific receptor. Herpesvirus vectors naturally target the cells of the central and peripheral nervous system. Alternatively, the route of administration can be used to target a specific cell or tissue. For example, intracoronary administration of an adenoviral vector has been shown to be effective for the delivery of a gene to cardiac myocytes (Maurice et al., *J. Clin. Invest.* 104:21 (1999)). Intravenous delivery of cholesterol-containing cationic liposomes has been shown to preferentially target pulmonary tissues (Liu et al., *Nature Biotechnol.* 15:167 (1997)), and effectively mediate transfer and expression of genes in vivo. Other examples of successful targeted in vivo delivery of nucleic acid molecules are known in the art. Finally, a recombinant nucleic acid molecule can be selectively (i.e., preferentially, substantially exclusively) expressed in a target cell by selecting a transcription control sequence, and preferably, a promoter, which is selectively induced in the target cell and remains substantially inactive in non-target cells.

In certain embodiments, the invention relates to a method of enhancing cardiac repair in a subject, comprising delivering a therapeutically effective amount of an agent that stimulates the Wnt/β-catenin pathway to the subject. The agent can be any agent that stimulates the Wnt/β-catenin pathway, directly or indirectly, at any point in the pathway that results in enhancement of cardiac repair. The agent can be any type of molecule, such as small molecules (compounds less than about 1000 Daltons), polypeptides (including enzymes, antibodies, and Fab' fragments), carbohydrates, lipids, coenzymes, and nucleic acid molecules (including DNA, RNA, and chimerics and analogs thereof, an antisense nucleic acid, an siRNA, or a ribozyme) and nucleotides and nucleotide analogs. Polypeptides that can stimulate the Wnt/β-catenin pathway include, without limitation, Wnt1, Dkk, crescent, Cerberus, axin, Frzb, glycogen synthase kinase, T-cell factor, or a dominant negative disheveled polypeptide, or any functional fragment or homolog thereof. Suitable small molecule agents that stimulate the Wnt/β-catenin pathway include, without limitation, BIO (6-bromoindirubin-3'-oxime), DCA (deoxycholic acid), and SB-216763 (Chen et al., *Am. J. Physiol. Gastrointesi. Liver. Physiol.* 299(2):G293-300. Epub 2010 May 27). Suitable agents also include inhibitors (e.g., an antibody, antisense oligonucleotide, siRNA, etc.) of any antagonist of the Wnt/β-catenin pathway such as Dickoppf and secreted frizzled related proteins or small molecules such as, but not limited to, niclosamide and 2,4-diaminoquinazoline).

The agent can be delivered to the subject by any suitable means, including systemically (e.g., intravenously or orally) or locally (e.g., directly to the heart).

III. Methods of Enhancing Angiogenesis

One aspect of the invention relates to a method of stimulating the proliferation of endothelial progenitor cells (EPC), comprising contacting the EPC with Wnt1. In certain embodiments, contacting the EPC with Wnt1 comprises contacting the EPC with Wnt1 polypeptide. In other embodiments, contacting the EPC with Wnt1 comprises modifying the EPC to recombinantly express Wnt1 polypeptide. The EPC may be contacted in vitro, ex vivo, and/or in vivo. In some embodiments, the EPC are isolated from a subject (e.g., from blood and/or bone marrow), contacted with Wnt1, and then returned to the subject (e.g., autologous donation) or delivered to a different subject (e.g., for cell therapy). The isolated EPC can be cultured to increase the number of cells before being returned to the subject. The contacting step can occur before, during, and or after the culturing of the cells. As Wnt1 increases the proliferation of EPC, the methods of the present invention provide a means to increase the number of EPC in a subject, e.g., a subject having ischemia and/or an abnormally low level of circulating EPC. Additionally, Wnt1 may improve the function of cultured EPC, e.g., dysfunctional EPC isolated from subjects with diabetes or heart disease. Thus, the present invention may be used not only to increase the number of EPC available for cell therapy, but also to increase the functional properties of the EPC used for cell therapy.

In another aspect, the invention relates to a method of increasing blood vessel formation in an ischemic tissue of a subject, comprising delivering Wnt1 to the ischemic tissue. Increasing blood vessel formation includes, without limitation, growth of new blood vessels (angiogenesis) and/or extension of existing blood vessels (arteriogenesis), and includes formation of capillaries, arteries, veins, and/or lymphatic vessels.

In an additional aspect, the invention relates to a method of increasing blood flow in an ischemic tissue of a subject, comprising delivering Wnt1 to the ischemic tissue.

In a further aspect, the invention relates to a method of treating ischemia in a tissue of a subject, comprising delivering Wnt1 to the ischemic tissue.

In certain embodiments of the above methods, delivering Wnt1 to the ischemic tissue comprises delivering Wnt1 polypeptide to the tissue. In other embodiments, delivering Wnt1 to the ischemic tissue comprises delivering a polynucleotide encoding Wnt1 polypeptide to the tissue. The ischemic tissue can be any tissue in the subject, including, without limitation, limbs (e.g., diabetic patients), brain (e.g., stroke patients), and heart (e.g., myocardial infract patients). In certain embodiments, the subject is one in need of increased angiogenesis and/or arteriogenesis. For example, the subject may be one that has experienced ischemia, is currently experiencing ischemia, or has a disorder or condition that is likely to lead to an ischemic event. In certain embodiments, the subject is one that has vascular deficiencies, cardiovascular disease, or would benefit from the stimulation of endothelial cell activation and stabilization of newly formed microvessels or other vessels. In certain embodiments, the subject is at risk for ischemia. In one embodiment, the subject has diabetes (e.g., type I or type II) or a pre-diabetic condition. The subject may be suffering from or at risk for one or more complications due to diabetes, such as nephropathy, retinopathy, coronary artery disease, peripheral vascular disease and associated ulcers, gangrene, and/or pain, and/or autonomic dysfunction. In other embodiments, the subject has a graft (e.g., a skin graft) or other transplanted tissue, an anastomosis, a wound, an ulcer, a burn, male pattern baldness, atherosclerosis, ischemic heart tissue, ischemic peripheral tissue (e.g., limb or mesentery ischemia), myocardial or cerebral infarction, or vascular occlusion or stenosis.

In one aspect of the invention, the invention relates to a method of increasing blood vessel formation in an ischemic tissue of a subject, comprising delivering to the ischemic tissue EPC, wherein the EPC have been contacted with Wnt1 and/or recombinantly express Wnt1.

In an additional aspect, the invention relates to a method of increasing blood flow in an ischemic tissue of a subject, comprising delivering to the ischemic tissue EPC, wherein the EPC have been treated with Wnt1 and/or recombinantly express Wnt1.

In a further aspect, the invention relates to a method of treating ischemia in a tissue of a subject, comprising delivering to the ischemic tissue EPC, wherein the EPC have been contacted with Wnt1 and/or recombinantly express Wnt1.

EPC can be contacted with Wnt1 and/or modified to recombinantly express Wnt1 as described above.

One aspect of the invention relates to an isolated EPC that has been contacted with Wnt1. The EPC can be contacted with Wnt1 before and/or after isolation. In some embodiments, the EPC is isolated from a subject and then contacted with Wnt1.

Another aspect of the invention relates to an isolated EPC that recombinantly expresses Wnt1.

In certain embodiments, the isolated EPC is a human EPC. In other embodiments, the Wnt1 is human Wnt1 or a functional fragment or homolog thereof.

IV. Polynucleotide, Vectors, and Cells

In those aspects of the invention related to recombinant expression of Wnt1, the Wnt1 can be encoded by a polynucleotide comprising, consisting essentially of or consisting of a nucleotide sequence that encodes Wnt1 polypeptide or a functional fragment thereof. Amino acid and nucleotide sequences of Wnt1 are well known in the art and are available in databases such as GenBank. Polynucleotides of this invention include RNA, DNA (including cDNAs) and chimeras thereof. The polynucleotides can further comprise modified nucleotides or nucleotide analogs. It will be appreciated by those skilled in the art that there can be variability in the polynucleotides that encode Wnt1 due to the degeneracy of the genetic code. The degeneracy of the genetic code, which allows different nucleic acid sequences to code for the same polypeptide, is well known in the literature.

The polynucleotides encoding Wnt1 will typically be associated with appropriate expression control sequences, e.g., promoters, enhancers, transcription/translation control signals and polyadenylation signals.

A variety of promoter/enhancer elements can be used depending on the level and tissue-specific expression desired. The promoter can be constitutive or inducible, depending on the pattern of expression desired. The promoter can be native or foreign and can be a natural or a synthetic sequence. By foreign, it is intended that the transcriptional initiation region is not found in the wild-type host into which the transcriptional initiation region is introduced. The promoter is chosen so that it will function in the target cell(s) of interest.

To illustrate, the polynucleotide encoding Wnt1 can be operatively associated with a cytomegalovirus (CMV) major immediate-early promoter, an albumin promoter, an Elongation Factor 1-α (EF1-α) promoter, a PγK promoter, a MFG promoter, or a Rous sarcoma virus promoter.

Inducible promoter/enhancer elements include hormone-inducible and metal-inducible elements, and other promoters regulated by exogenously supplied compounds, including without limitation, the zinc-inducible metallothionein (MT) promoter; the dexamethasone (Dex)-inducible mouse mammary tumor virus (MMTV) promoter; the T7 polymerase promoter system (see WO 98/10088); the ecdysone insect promoter (No et al., *Proc. Natl. Acad. Sci. USA* 93:3346 (1996)); the tetracycline-repressible system (Gossen et al., *Proc. Natl. Acad. Sci. USA* 89:5547 (1992)); the tetracycline-inducible system (Gossen et al., *Science* 268:1766 (1995); see also Harvey et al., *Curr. Opin. Chem. Biol.* 2:512 (1998)); the RU486-inducible system (Wang et al., *Nat. Biotech.* 15:239 (1997); Wang et al., *Gene Ther.*, 4:432 (1997)); and the rapamycin-inducible system (Magari et al., *J. Clin. Invest.* 100: 2865 (1997)).

Moreover, specific initiation signals are generally required for efficient translation of inserted protein coding sequences. These translational control sequences, which can include the ATG initiation codon and adjacent sequences, can be of a variety of origins, both natural and synthetic.

The present invention further provides cells comprising the polynucleotides and polypeptides of the invention. The cell may be a cultured cell or a cell ex vivo or in vivo, e.g., for use in therapeutic methods, diagnostic methods, screening methods, methods for studying the biological action of polypeptides, methods of producing polypeptides, or methods of maintaining or amplifying the polynucleotides of the invention, etc. The cell can be e.g., a bacterial, fungal (e.g., yeast), plant, insect, avian, mammalian, or human cell.

The polynucleotide can be incorporated into an expression vector. Expression vectors compatible with various host cells are well known in the art and contain suitable elements for transcription and translation of nucleic acids. Typically, an expression vector contains an "expression cassette," which includes, in the 5' to 3' direction, a promoter, a coding sequence encoding a polypeptide operatively associated with the promoter, and, optionally, a termination sequence including a stop signal for RNA polymerase and a polyadenylation signal for polyadenylase.

Non-limiting examples of promoters of this invention include CYC1, HIS3, GAL1, GAL4, GAL10, ADH1, PGK, PHO5, GAPDH, ADC1, TRP1, URA3, LEU2, ENO, TPI, and alkaline phosphatase promoters (useful for expression in *Saccharomyces*); AOX1 promoter (useful for expression in *Pichia*); β-lactamase, lac, ara, tet, trp, $IP_L$, $IP_R$, T7, tac, and trc promoters (useful for expression in *Escherichia coli*); light regulated-, seed specific-, pollen specific-, ovary specific-, pathogenesis or disease related-promoters, cauliflower mosaic virus 35S, CMV 35S minimal, cassaya vein mosaic virus (CsVMV), chlorophyll a/b binding protein, ribulose 1,5-bisphosphate carboxylase, shoot-specific promoters, root specific promoters, chitinase, stress inducible promoters, rice tungro bacilliform virus, plant super-promoter, potato leucine aminopeptidase, nitrate reductase, mannopine synthase, nopaline synthase, ubiquitin, zein protein, and anthocyanin promoters (useful for expression in plant cells).

Further examples of animal and mammalian promoters known in the art include, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, baculovirus IE1 promoter, elongation factor 1 alpha (EF1) promoter, phosphoglycerate kinase (PGK) promoter, ubiquitin (Ubc) promoter, an albumin promoter, the regulatory sequences of the mouse metallothionein-L promoter and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis and/or disease-related promoters, and promoters that exhibit tissue specificity, such as the elastase I gene control region, which is active in pancreatic acinar cells; the insulin gene control region active in pancreatic beta cells, the immunoglobulin gene control region active in lymphoid cells, the mouse mammary tumor virus control region active in testicular, breast, lymphoid and mast cells; the albumin gene promoter, the Apo AI and Apo AII control regions active in liver, the alpha-fetoprotein gene control region active in liver, the alpha 1-antitrypsin gene control region active in the liver, the beta-globin gene control region active in myeloid cells, the myelin basic protein gene control region active in oligodendrocyte cells in the brain, the myosin light chain-2 gene control region active in skeletal muscle, the gonadotropic releasing hormone gene control region active in the hypothalamus, the pyruvate kinase promoter, the villin promoter, the promoter of the fatty acid binding intestinal protein, the promoter of smooth muscle cell α-actin, and the like. In addition, any of these expression sequences of this invention can be modified by addition of enhancer and/or regulatory sequences and the like.

Enhancers that may be used in embodiments of the invention include but are not limited to: an SV40 enhancer, a cytomegalovirus (CMV) enhancer, an elongation factor I (EF1) enhancer, yeast enhancers, viral gene enhancers, and the like.

Termination control regions, i.e., terminator or polyadenylation sequences, may be derived from various genes native to the preferred hosts. In some embodiments of the invention, the termination control region may comprise or be derived from a synthetic sequence, a synthetic polyadenylation signal, an SV40 late polyadenylation signal, an SV40 polyadenylation signal, a bovine growth hormone (BGH) polyadenylation signal, viral terminator sequences, or the like.

Expression vectors can be designed for expression of polypeptides in host cells, e.g., prokaryotic or eukaryotic cells. For example, polypeptides can be expressed in bacterial cells such as E. coli, insect cells (e.g., the baculovirus expression system), yeast cells, plant cells or mammalian cells. Some suitable host cells are discussed further in Goeddel, *Gene Expression Technology*: Methods in Enzymology 185, Academic Press, San Diego, Calif. (1990). Examples of bacterial vectors include pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, and pRIT5 (Pharmacia). Examples of vectors for expression in the yeast *S. cerevisiae* include pYepSec1 (Baldari et al., *EMBO J.* 6:229 (1987)), pMFa (Kurjan and Herskowitz, *Cell* 30:933 (1982)), pJRY88 (Schultz et al., *Gene* 54:113 (1987)), and pYES2 (Invitrogen Corporation, San Diego, Calif.). Baculovirus vectors available for expression of nucleic acids to produce proteins in cultured insect cells (e.g., Sf 9 cells) include the pAc series (Smith et al., *Mol. Cell. Biol.* 3:2156 (1983)) and the pVL series (Lucklow and Summers, *Virology* 170:31 (1989)).

Examples of mammalian expression vectors include pWL-NEO, pSV2CAT, pOG44, pXT1, pSG (Stratagene) pSVK3, PBPV, pMSG, PSVL (Pharmacia), pCDM8 (Seed, *Nature* 329:840 (1987)), pMT2PC (Kaufman et al., *EMBO J.* 6:187 (1987)), Gateway® and pcDNA™ vectors (Invitrogen), Checkmate™/Flexi®, pCAT® and HaloTag™ vectors (Promega). When used in mammalian cells, the expression vector's control functions are often provided by viral regulatory elements. For example, commonly used promoters are derived from polyoma, adenovirus 2, cytomegalovirus and Simian Virus 40.

Viral vectors have been used in a wide variety of gene delivery applications in cells, as well as living animal subjects. Viral vectors that can be used include, but are not limited to, retrovirus, lentivirus, adeno-associated virus, poxvirus, alphavirus, baculovirus, vaccinia virus, herpes virus, Epstein-Barr virus, adenovirus, geminivirus, and caulimovirus vectors. Non-viral vectors include plasmids, liposomes, electrically charged lipids (cytofectins), nucleic acid-protein complexes, and biopolymers. In addition to a nucleic acid of interest, a vector may also comprise one or more regulatory regions, and/or selectable markers useful in selecting, measuring, and monitoring nucleic acid transfer results (delivery to specific tissues, duration of expression, etc.).

In addition to the regulatory control sequences discussed above, the recombinant expression vector can contain additional nucleotide sequences. For example, the recombinant expression vector can encode a selectable marker gene to identify host cells that have incorporated the vector.

Vector DNA can be introduced into prokaryotic or eukaryotic cells via conventional transformation or transfection techniques, including, without limitation, calcium phosphate or calcium chloride co-precipitation, DEAE-dextran-mediated transfection, lipofection, electroporation, microinjection, DNA-loaded liposomes, lipofectamine-DNA complexes, cell sonication, gene bombardment using high velocity microprojectiles, and viral-mediated transfection. Suitable methods for transforming or transfecting host cells can be found in Sambrook et al., Molecular Cloning: A Laboratory Manual 2nd Ed. (Cold Spring Harbor, N.Y., 1989), and other laboratory manuals.

If stable integration is desired, often only a small fraction of cells (in particular, mammalian cells) integrate the foreign DNA into their genome. In order to identify and select integrants, a nucleic acid that encodes a selectable marker (e.g., resistance to antibiotics) can be introduced into the host cells along with the nucleic acid of interest. Preferred selectable markers include those that confer resistance to drugs, such as G418, hygromycin and methotrexate. Nucleic acids encoding a selectable marker can be introduced into a host cell on the same vector as that comprising the nucleic acid of interest or can be introduced on a separate vector. Cells stably transfected with the introduced nucleic acid can be identified by drug selection (e.g., cells that have incorporated the selectable marker gene will survive, while the other cells die).

The polynucleotide can also be introduced into a plant, plant cell or protoplast and, optionally, the isolated nucleic acid encoding the polypeptide is integrated into the nuclear or plastidic genome. Plant transformation is known in the art. See, in general, *Meth. Enzymol.* Vol. 153 ("Recombinant DNA Part D") 1987, Wu and Grossman Eds., Academic Press and European Patent Application EP 693554.

According to certain embodiments, the polynucleotides or vectors can be targeted to specific cells or tissues in vivo as described above.

V. Pharmaceutical Compositions

As a further aspect, the invention provides pharmaceutical formulations and methods of administering the same to achieve any of the therapeutic effects (e.g., cardiac repair or stimulation of angiogenesis) discussed above. The pharmaceutical formulation may comprise any of the reagents discussed above in a pharmaceutically acceptable carrier, e.g., a Wnt1 polypeptide or a fragment or homolog thereof, a polynucleotide encoding a Wnt1 polypeptide or a fragment or homolog thereof, or a cell expressing a Wnt1 polypeptide or a fragment or homolog thereof, or an antisense oligonucleotide, an siRNA molecule, a ribozyme, an aptamer, a peptidomimetic, an antibody, a small molecule, or any other compound that modulates the activity of the Wnt1/β-catenin pathway.

By "pharmaceutically acceptable" it is meant a material that is not biologically or otherwise undesirable, i.e., the material can be administered to a subject without causing any undesirable biological effects such as toxicity.

The formulations of the invention can optionally comprise medicinal agents, pharmaceutical agents, carriers, adjuvants, dispersing agents, diluents, and the like.

The agents of the invention can be formulated for administration in a pharmaceutical carrier in accordance with known techniques. See, e.g., Remington, *The Science And Practice of Pharmacy* (9$^{th}$ Ed. 1995). In the manufacture of a pharmaceutical formulation according to the invention, the agent is typically admixed with, inter alia, an acceptable carrier. The carrier can be a solid or a liquid, or both, and is preferably formulated with the agent as a unit-dose formulation, for example, a tablet, which can contain from 0.01 or 0.5% to 95% or 99% by weight of the compound. One or more agents can be incorporated in the formulations of the invention, which can be prepared by any of the well-known techniques of pharmacy.

A further aspect of the invention is a method of treating subjects in vivo, comprising administering to a subject a pharmaceutical composition comprising an agent of the invention in a pharmaceutically acceptable carrier, wherein the pharmaceutical composition is administered in a therapeutically effective amount. Administration of the agents of the present invention to a human subject or an animal in need thereof can be by any means known in the art for administering agents.

The formulations of the invention include those suitable for oral, rectal, topical, buccal (e.g., sub-lingual), vaginal, parenteral (e.g., subcutaneous, intramuscular including skeletal muscle, cardiac muscle, diaphragm muscle and smooth muscle, intradermal, intravenous, intraperitoneal), topical (i.e., both skin and mucosal surfaces, including airway surfaces), intranasal, transdermal, intraarticular, intrathecal, and inhalation administration, administration to the liver by intraportal delivery, as well as direct organ injection (e.g., into the heart, into the liver, into the brain for delivery to the central nervous system, into the pancreas, or into a tumor or the tissue surrounding a tumor). The most suitable route in any given case will depend on the nature and severity of the condition being treated and on the nature of the particular agent which is being used. In some embodiments, it may be desirable to deliver the formulation locally to avoid any side effects associated with systemic administration. For example, local administration can be accomplished by direct injection at the desired treatment site, by introduction intravenously at a site near a desired treatment site (e.g., into a vessel that feeds a treatment site), or directly to the wall of a vessel (e.g., using a drug delivery catheter such as a balloon catheter). In some embodiments, the formulation can be delivered locally to ischemic tissue. In certain embodiments, the formulation can be a slow release formulation, e.g., in the form of a slow release depot.

For injection, the carrier will typically be a liquid, such as sterile pyrogen-free water, pyrogen-free phosphate-buffered saline solution, bacteriostatic water, or Cremophor EL[R] (BASF, Parsippany, N.J.). For other methods of administration, the carrier can be either solid or liquid.

For oral administration, the agent can be administered in solid dosage forms, such as capsules, tablets, and powders, or in liquid dosage forms, such as elixirs, syrups, and suspensions. Agents can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for buccal (sub-lingual) administration include lozenges comprising the agent in a flavored base, usually sucrose and acacia or tragacanth; and pastilles comprising the agent in an inert base such as gelatin and glycerin or sucrose and acacia.

Formulations of the present invention suitable for parenteral administration comprise sterile aqueous and non-aqueous injection solutions of the agent, which preparations are preferably isotonic with the blood of the intended recipient. These preparations can contain anti-oxidants, buffers, bacteriostats and solutes which render the formulation isotonic with the blood of the intended recipient. Aqueous and non-aqueous sterile suspensions can include suspending agents and thickening agents. The formulations can be presented in unit\dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, in one aspect of the present invention, there is provided an injectable, stable, sterile composition comprising an agent of the invention, in a unit dosage form in a sealed container. The agent is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the agent. When the agent is substantially water-insoluble, a sufficient amount of emulsifying agent which is pharmaceutically acceptable can be employed in sufficient quantity to emulsify the agent in an aqueous carrier. One such useful emulsifying agent is phosphatidyl choline.

Formulations suitable for rectal administration are preferably presented as unit dose suppositories. These can be prepared by admixing the agent with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which can be used include petroleum jelly, lanoline, polyethylene glycols, alcohols, transdermal enhancers, and combinations of two or more thereof.

Formulations suitable for transdermal administration can be presented as discrete patches adapted to remain in intimate contact with the epidermis of the recipient for a prolonged period of time. Formulations suitable for transdermal administration can also be delivered by iontophoresis (see, for example, Tyle, *Pharm. Res.* 3:318 (1986)) and typically take the form of an optionally buffered aqueous solution of the agent. Suitable formulations comprise citrate or bis\tris buffer (pH 6) or ethanol/water and contain from 0.1 to 0.2M of the agent.

The agent can alternatively be formulated for nasal administration or otherwise administered to the lungs of a subject by any suitable means, e.g., administered by an aerosol suspension of respirable particles comprising the agent, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raeburn et al., *J. Pharmacol. Toxicol. Meth.* 27:143 (1992). Aerosols of liquid particles comprising the compound can be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the agent can likewise be produced with any solid particulate medicament aerosol generator, by techniques known in the pharmaceutical art.

Alternatively, one can administer the agent in a local rather than systemic manner, for example, in a depot or sustained-release formulation.

Further, the present invention provides liposomal formulations of the agents disclosed herein. The technology for forming liposomal suspensions is well known in the art. When the agent is an aqueous-soluble salt, using conventional liposome technology, the same can be incorporated into lipid vesicles. In such an instance, due to the water solubility of the agent, the agent will be substantially entrained within the hydrophilic center or core of the liposomes. The lipid layer employed can be of any conventional composition and can either contain cholesterol or can be cholesterol-free. When the agent of interest is water-insoluble, again employing conventional liposome formation technology, the agent can be substantially entrained within the hydrophobic lipid bilayer which forms the structure of the liposome. In either instance, the liposomes which are produced can be reduced in size, as through the use of standard sonication and homogenization techniques.

The liposomal formulations containing the agents disclosed herein, can be lyophilized to produce a lyophilizate which can be reconstituted with a pharmaceutically acceptable carrier, such as water, to regenerate a liposomal suspension.

In the case of water-insoluble agents, a pharmaceutical composition can be prepared containing the water-insoluble agent, such as for example, in an aqueous base emulsion. In such an instance, the composition will contain a sufficient amount of pharmaceutically acceptable emulsifying agent to emulsify the desired amount of the agent. Particularly useful emulsifying agents include phosphatidyl cholines and lecithin.

In particular embodiments, the agent is administered to the subject in a therapeutically effective amount, as that term is defined above. Dosages of pharmaceutically active agents can be determined by methods known in the art, see, e.g., *Remington's Pharmaceutical Sciences* (Maack Publishing Co., Easton, Pa.). The therapeutically effective dosage of any specific agent will vary somewhat from agent to agent, and patient to patient, and will depend upon the condition of the patient and the route of delivery. As a general proposition, a dosage from about 0.1 to about 50 mg/kg will have therapeutic efficacy, with all weights being calculated based upon the weight of the agent. Toxicity concerns at the higher level can restrict intravenous dosages to a lower level such as up to about 10 mg/kg, with all weights being calculated based upon the weight of the agent. A dosage from about 10 mg/kg to about 50 mg/kg can be employed for oral administration. Typically, a dosage from about 0.5 mg/kg to 5 mg/kg can be employed for intramuscular injection. Particular dosages are about 1 µmol/kg to 50 µmol/kg, and more particularly to about 22 µmol/kg and to 33 µmol/kg of the agent for intravenous or oral administration, respectively.

In particular embodiments of the invention, more than one administration (e.g., two, three, four, or more administrations) can be employed over a variety of time intervals (e.g., hourly, daily, weekly, monthly, etc.) to achieve therapeutic effects.

The present invention finds use in research and therapeutic applications, including veterinary and medical applications. Suitable subjects include both avians and mammals, with mammals being preferred. The term "avian" as used herein includes, but is not limited to, chickens, ducks, geese, quail, turkeys, and pheasants. The term "mammal" as used herein includes, but is not limited to, humans, bovines, ovines, caprines, equines, felines, canines, lagomorphs, etc. Human subjects include neonates, infants, juveniles, and adults. In other embodiments, the subject is an animal model of ischemia. In certain embodiments, the subject has or is at risk for diabetes (e.g., Type I or Type II diabetes). In other embodiments, the subject has cardiovascular disease or has experienced ischemia or stroke. In still other embodiments, the subject is at risk for ischemia. In further embodiments, the subject is in need of increase angiogenesis and/or arteriogenesis.

The present invention is more particularly described in the following examples that are intended as illustrative only since numerous modifications and variations therein will be apparent to those skilled in the art.

EXAMPLE 1

Materials and Methods

Myocardial Injury

Mice were anesthetized with isoflurane and a left thoracotomy was performed under mechanical ventilation using a volume cycled Harvard Rodent ventilator. Under direct visualization, the pericardial sac was opened and the LAD artery was ligated close to its origin with a 6-0 suture. Myocardial ischemia was confirmed by myocardial blanching as well as ST elevation on continuous ECG monitoring. Following 30 minutes of ischemia, the suture was released to induce reperfusion injury and this was confirmed by decreased ST segment elevation on ECG. Body temperatures of the animals were monitored with a rectal probe and maintained by using a heated surgical platform. The chest wall was closed in layers and the mice were transferred onto a temperature controlled pad for recovery.

In Situ Hybridization

For in-situ hybridization, a mouse Wnt1 cDNA fragment (460-1377 bp) was subcloned into pKanascript vector, linearized with SafI and XbaI to prepare probes by in-vitro transcription (Avantaggiato et al., *Dev. Biol.* 175:347 (1996)). Digoxigenin probes were synthesized using DIG-UTP labeling kit (Roche). Probes were validated by staining areas of mouse embryo known to express Wnt1 and sense strand controls were used in parallel. Harvested hearts were perfused with RNAse free PBS, and frozen in OCT. ISH was performed on 7 µm cryo-sections.

Generation of Col1a2-CreER (T)/β-catenin$^{fl/fl}$ Mice

Col1a2-CreER(T)/0 mice carry a tamoxifen-inducible Cre-recombinase [CreER(T)] under the control of a fibroblast-specific regulatory sequence from the proα2(I) collagen gene [C57BL/6J-Tg(Col1a2-CreER(T))] (Kapoor et al., *J.*

*Clin. Invest.* 118:3279 (2008)). Col1a2-CreER(T)/0 were crossed with β-catenin$^{fl/fl}$ mice (Jackson Labs) to generate Col1a2-CreER(T)/βcatenin$^{fl/fl}$ mice, that were used in experiments. To delete β-catenin, adult mice (age, 6-7 weeks) were given intraperitoneal injections of the tamoxifen suspension (0.1 ml of 10 mg/ml) for 10 days and injections were stopped 5 days before surgery. Following surgery, tamoxifen was administered for another 5 days. All surgical procedures were approved by IACUC at the University of North Carolina at Chapel Hill, N.C.

Quantitative RT-PCR

Total RNA from mouse heart, or cell was isolated with SV Total RNA Isolation system by following the manufacturer's protocols (Promega). qPCR reactions (including no "RT control"), were performed at least in triplicate. The reactions were performed at 95° C. for 10 min, followed by 40 cycles of 95° C. for 15 s and 60° C. for 60 s. Fold changes in gene expression were calculated using the ΔΔCt method after normalizing to GAPDH. Wnt primer sequences were used as previously described (Kemp et al., *Dev. Dyn.* 233:1064 (2005)).

Xgal Staining

In brief, whole hearts were harvested and fixed in 0.2% glutaraldehyde solution at 4° C. for 4 hrs. The fixed hearts were used for whole mount staining or embedded in OCT compound and frozen for tissue section. Cryo-sections (15 and 7 μm) were prepared and stained for β-galactosidase activity (Lobe et al., *Dev. Biol.* 208:281 (1999)).

Echocardiography

Echocardiography was performed using a Visualsonic Ultrasound System (Vevo 2100). Parasternal short-axis and long-axis 2D and M-mode views were recorded. The long-axis view was used for measurement of cardiac parameters. End-diastolic and end-systolic interventricular septum (IVSd, IVSs), posterior wall thickness (PWTd, PWTs) and left ventricular internal diameters (LVEDD, LVESD) were calculated and averaged from three consecutive contractions using Visual Sonics software. Left ventricular systolic function was assessed by ejection fraction (% EF=[(EDv−ESv)/EDv]×100) and fractional shortening (% FS=[(LVEDD−LVESD)/LVEDD]×100). The observer was blinded to the genotype and type of procedure performed on the mice.

Epicardium Cell Isolation

Timed matings were performed to harvest E12.5 dpf embryos for isolation of epicardial cells as described (Dong et al. *Methods Enzymol.* 445:209 (2008)).

Cardiac Fibroblast Isolation and Proliferation Assays

Briefly, 8 week old adult mouse hearts were excised, minced and placed in a solution containing 50 U/ml Collagenase II and 0.1% trypsin. Cardiac fibroblasts were further isolated and cultured by standard methods (Gustafsson et al., *Mol. Pharmacol.* 58:1470 (2000)). All cells used in experiments were from passages 2 or 3. The purity of these cultures was determined by immunofluorescent staining with vimentin and DDR2 antibodies. The proliferation of isolated cardiac fibroblasts was assayed by CyQUANT cell proliferation assay kit (Invitrogen) and FITC BrdU Flow Kit (BD biosciences) as described by the manufacturer's protocols. For CyQUANT proliferation assays, cardiac fibroblasts were seeded at a density of $4\times10^3$ cells/well in 48 well plates a day prior to Wnt1 treatment.

Epicardium Cell Wound Migration Assay

Epicardial cells were harvested on gelatin coated 24-well plates. The monolayer was injured by scratching across the epicardial colony with a 20 μl pipette tip. After washing, the cells were then cultured in 3% FBS medium with/without Wnt1 protein (25 nM) (ABCAM, MA, USA). Scratch wound distance was measured using WCIF image J software.

Construction of Plasmids and Lentiviruses

The pLenti6/V5-DEST Gateway® Vector system was used for lentiviruses cloning and lentiviruses were produced by the Vector Core Facility at the University of North Carolina at Chapel Hill.

Histology

Whole hearts were harvested and fixed with 2% paraformaldehyde at 4° C. for 24 hrs. Fixed tissues were dehydrated, embedded in paraffin and 5-7 μm thickness sections prepared. Masson's trichrome staining was performed using standard techniques.

EXAMPLE 2

Dynamic Wnt1 Expression from Epicardium to Injury Region

Figure 1:
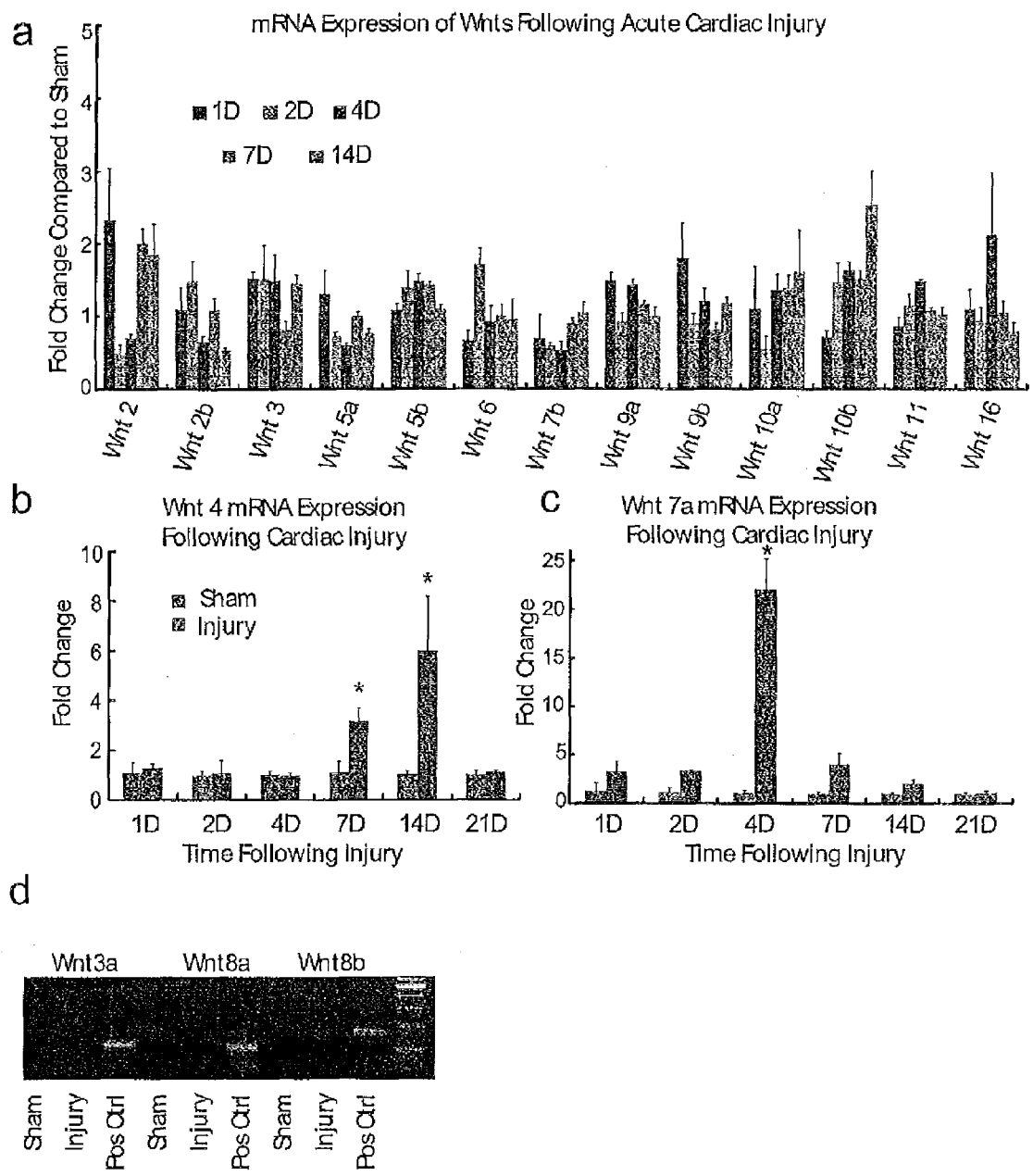
FIGS. 1a-1d show expression of Wnts after acute cardiac injury. (a) Screening of Wnts at different time points following acute cardiac injury; (b) Expression of Wnt4; and (c) Wnt7A shows temporally separated peaks; (d) Wnts that are not expressed in the heart with/without injury; Pos Ctrl refers to ES cells that express these Wnts (n=8 animals/group, *p<0.05 compared to sham; mean±SEM).
Figure 2:
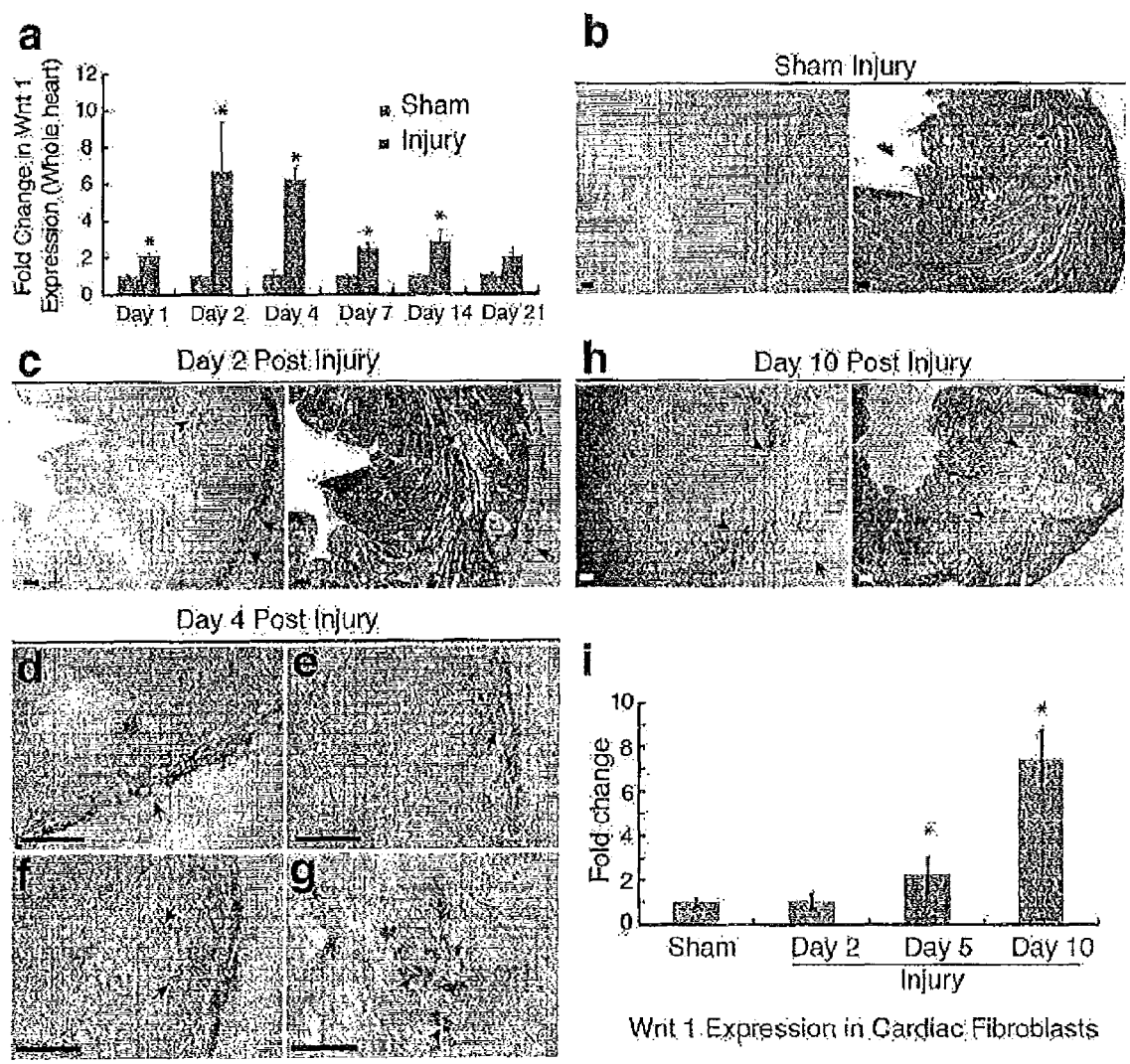
FIGS. 2a-2i show Wnt1 expression in the injured heart. (a) qPCR of Wnt1 expression in whole hearts following injury (n=8 animals/group, *p<0.05 versus sham; mean±SEM); (b) Sham injured heart with in-situ hybridization (ISH) for Wnt1 and Masson trichrome (MT) staining of same; (c) Wnt1 ISH day 2 post injury (arrows show epicardium and arrowhead region of injury) and MT staining of same; (d-g) Wnt1 ISH day 4 post injury: (d) Wnt1 expression in epicardial cells (arrow); (e) early invasion of Wnt1 expression (arrow); (f) contiguous Wnt1 expression into adjoining myocardium (arrow); (g) Wnt1 expression in region of injury (arrowhead); (h) Wnt1 ISH day 10 post injury; Wnt1 expression in area of injury (arrowhead) and absence of Wnt1 expression in the epicardium (arrow) with MT staining of same; (i) qPCR of Wnt1 expression in cardiac fibroblasts isolated following injury (n=3 animals/group *p<0.05 compared to sham; mean±SEM). Scale bar: 100 µm.

Changes in expression of all 19 mammalian Wnts by quantitative PCR (qPCR) were screened at different time points following acute ischemic cardiac injury (FIG. 1a). Expression of most Wnts in the heart was low and did not change significantly following injury (FIG. 1a), while some Wnts were not expressed at all (FIG. 1d). Wnt1, Wnt4 and Wnt7A expression significantly increased following injury (FIG. 2a; FIGS. 1b, 1c). Wnt7A exhibited a transient increase and sharp decline (FIG. 1c) while Wnt4 expression peaked at 14 days following injury (FIG. 1b). In contrast, Wnt1 expression increased by 7 fold within 2 days of acute cardiac injury and remained persistently elevated even at 14 days albeit at lower levels (FIG. 2a). As cardiac fibroblast recruitment, proliferation and an acute repair response occurs within the first several days following myocardial injury (Sun of al., *Cardiovasc. Res.* 46:250 (2000)), focus was placed on the possible role of Wnt1 in contributing to an active cardiac repair response.

To determine the anatomical region of expression of Wnt1, in-situ hybridization (ISH) to Wnt1 mRNA was performed following acute cardiac injury. Wnt1 was not expressed in sham injured animals (FIG. 2b). However, 2 days following injury, intense Wnt1 expression was surprisingly observed localizing to the epicardial and subepicardial space (FIG. 2c). Spotty Wnt1 expression was seen in the area of injury as well (FIG. 2c). At 4 days following injury, Wnt1 expression in the epicardium was again observed that had now expanded (FIG. 2d). Pockets of contiguous Wnt1 expression were seen extending from the epicardium into the adjoining myocardial interstitium (FIGS. 2e, 2f). Wnt1 expression in the region of injury was more intense compared to expression of Wnt1 in the injury at day 2 (FIG. 2g). By 10 days following injury, no expression of Wnt1 was seen in the epicardium and Wnt1 expression in its entirety was now localized to the region of injury (FIG. 2h).

Given the progressive localization of Wnt1 expression from the epicardium to the region of injury by 10 days, it was speculated that Wnt1 was likely expressed by cardiac fibroblasts. Cardiac fibroblasts were isolated and, consistent with ISH, significant up-regulation of Wnt1 was observed in fibroblasts isolated from injured hearts (FIG. 2i). Taken together these observations demonstrating up-regulation as well as localization of Wnt1 expression from the epicardium to the region of injury suggest a dynamic role of Wnt1 in activating the epicardium and cardiac fibroblasts following acute ischemic cardiac injury.

EXAMPLE 3

Wnt1 is Expressed by Epicardial Cells and Cardiac Fibroblasts

To confirm the phenotype of Wnt1 expressing cells, Wnt1Cre transgenic mice were crossed with the lineage reporter Rosa26R$^{lacZ}$ mice (Wnt1 cells express lacZ). Acute cardiac injury was induced in Wnt1Cre/R26R$^{lacZ}$ mice and lacZ expression analyzed in injured hearts.

Figure 4:
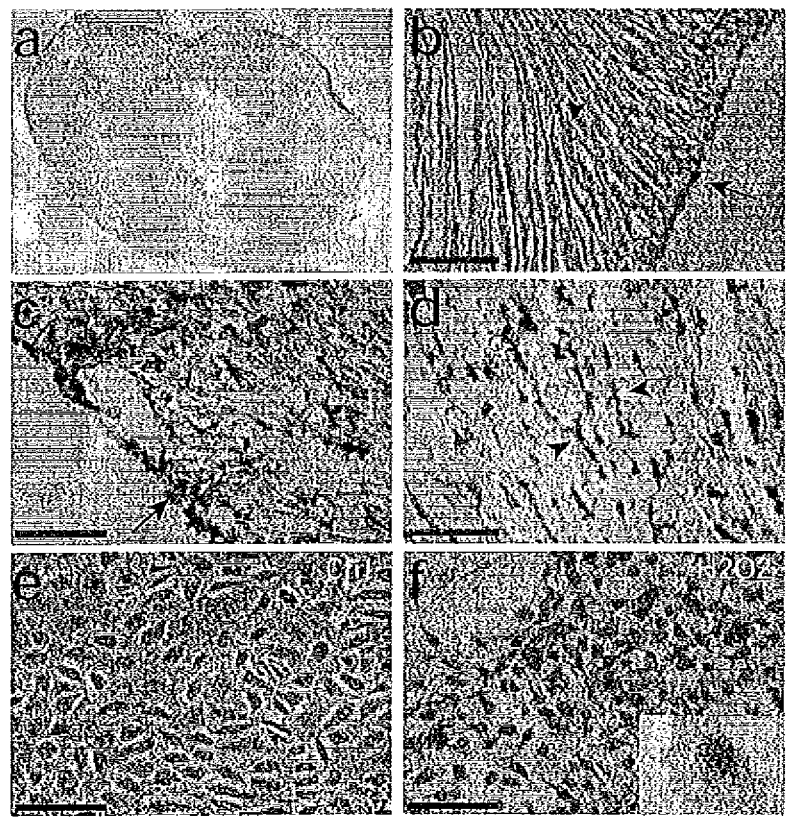
FIGS. 4a-4f show LacZ expression in Wnt1 Cre/R26R$^{lacZ}$ mice after cardiac injury. (a) Xgal staining of sham injured heart; and (b) higher magnification (arrow points to rare lacZ expressing epicardial cell and arrowhead to lacZ expressing cell in myocyte interstitium); (c-d) Xgal staining of heart day 2 post injury with abundant staining of epicardial cells (arrow) as well as cells (arrowhead) in myocyte interstitium in region of injury; (e-f) epicardial cells isolated from E12.5 dpf Wnt1Cre/R26R$^{lacZ}$ mice demonstrating Xgal staining of (e) untreated control cells (f) cells treated with $H_2O_2$ (f inset) epicardial colony in lower magnification. Scale bar: 100 µm.

Sham injured animals exhibited lacZ expression in the proximal aortic arch (Jiang et al., *Development* 127:1607 (2000)) as well as in cardiac nerves (Nakamura et al., *Circ. Res.* 98:1547 (2006)) (FIG. 3a). Sections showed minimal Xgal staining (FIG. 4a) with only rare epicardial and interstitial cells expressing lacZ (FIG. 4b). Wnt1 was dramatically expressed within 2 days of cardiac injury with strong lacZ expression observed in epicardial cells (FIG. 4c) and cells in the myocyte interstitium in the region of injury (FIG. 4d). At 7 and 10 days following injury, Wnt1 cells were predominantly present in the injured region (FIG. 3b). To corroborate that Wnt1 in the region of injury was expressed by cardiac fibroblasts, cardiac fibroblasts were isolated from Wnt1Cre/R26R$^{lacZ}$ mice following injury, and it was observed that cardiac fibroblasts that stained with β-galactosidase also stained for the cardiac fibroblast marker DDR2 (Goldsmith et al., Dev. Dyn. 230:787 (2004)) but not in sham injured animals (FIGS. 3c, 3d).

Next, the mechanism of Wnt1 up-regulation in epicardial cells following ischemia-reperfusion cardiac injury was determined. Acute ischemia-reperfusion injury of the heart is associated with generation of free radicals and it was investigated whether reactive oxygen species (ROS) could switch on Wnt1 transcription. Epicardial cells were isolated from E12.5 dpf Wnt1Cre/R26R$^{lacZ}$ embryos, treated with hydrogen peroxide (100 µM) For 10 minutes and stained for lacZ expression 24 hours later. Untreated control epicardial cells after 24 hours did not express lacZ (FIG. 4e); however upon brief treatment with hydrogen peroxide, the epicardial colony stained with Xgal (FIG. 4f, inset); demonstrating that increased ROS is a potential mechanism of Wnt1 up-regulation in vivo.

EXAMPLE 4

The Epicardium and Cardiac Fibroblasts are Wnt Responsive

Figure 5:
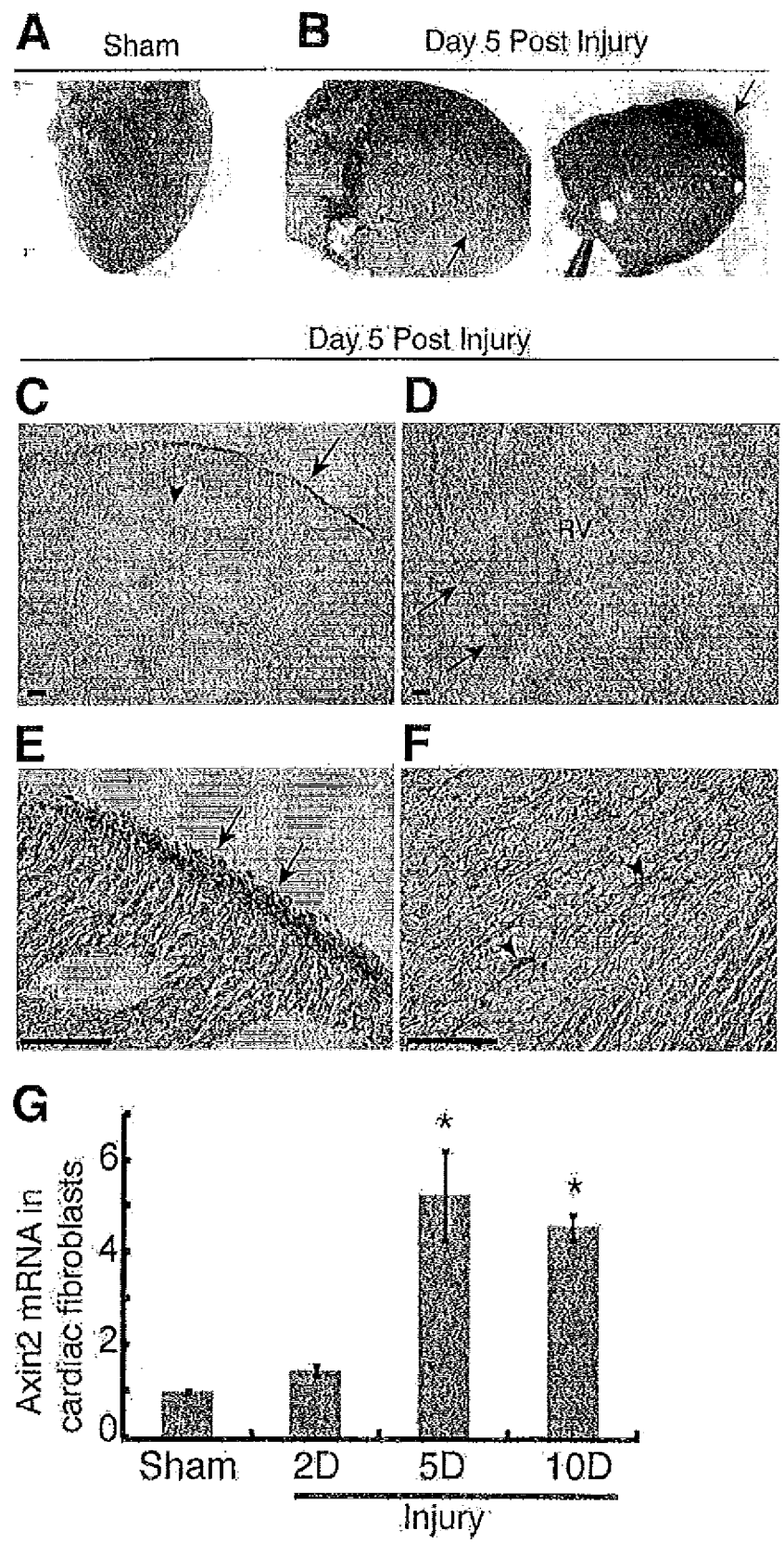
FIGS. 5a-5g show the epicardium and cardiac fibroblasts are Wnt responsive following acute cardiac injury. Hearts of TOPGAL transgenic mice (n=4 animals/group) stained with Xgal in whole mount (a) sham injured; (b) day 5 post injury with staining on cardiac surface (arrows); (c-f) day 5 post injury heart section shows (c) lacZ expression in epicardium (arrow) and area of injury (arrowhead); (d) staining of the epicardium (arrow) over the uninjured right ventricle (RV); (e) higher magnification of epicardium shows expansion of lacZ positive epicardial cells (arrow); (f) presence of lacZ expressing cells in the injury border zone (arrowhead); (g) qPCR for Axin2 expression in cardiac fibroblasts isolated at different time points following injury (n=3, *p<0.05 versus sham; mean±SEM). Scale bar: 100 µm.
Figure 6:
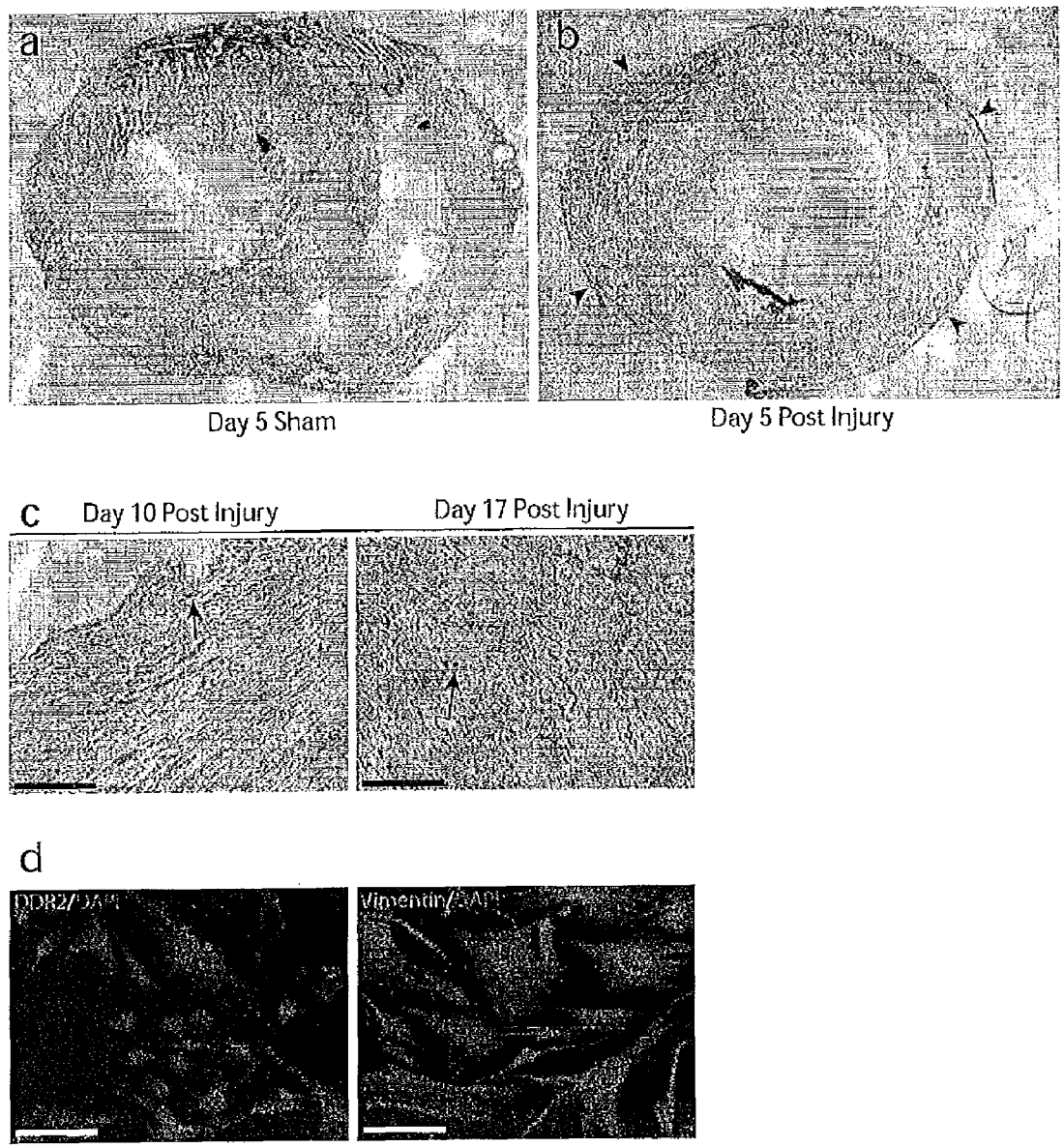
FIGS. 6a-6d show the epicardium organ-wide is Wnt responsive after cardiac injury. Xgal staining of TOPGAL mouse heart section 5 days following (a) sham or (b) ischemia-reperfusion injury demonstrating lacZ expressing epicardium circumferentially present around the ventricular surface of the heart (arrowheads); (c) Xgal staining 10 days and 17 days following injury shows scattered lacZ expressing cells (arrow); (d) DDR$^2$ and Vimentin staining to confirm phenotype of isolated cardiac fibroblasts. Scale bar: 100 µm.

As the epicardium expresses Wnt1 following cardiac injury, it was investigated whether the epicardium is also Wnt responsive following injury. TOPGAL transgenic mice were used that express lacZ driven by TCF4 response elements, TCF4 being a downstream mediator of canonical Wnt signaling (DasGupta et al., *Development* 126:4557 (1999)). Acute cardiac injury was induced in 8 week old TOPGAL transgenic mice and hearts of mice analyzed for lacZ expression. Sham injured hearts did not express lacZ (FIG. 5a). However within 5 days of cardiac injury, intense lacZ expression was visible on the surface of injured hearts (FIG. 5b). Analysis of heart sections demonstrated organ wide epicardial activation with the entire epicardium staining with Xgal (FIG. 6b) but not in sham injured hearts (FIG. 6a). The epicardium over both the injured left ventricle as well as the non-injured right ventricle was Wnt responsive (FIGS. 5c, 5d) with dramatic epicardial cell expansion (FIG. 5e). LacZ expression was also observed in the injury region (FIGS. 5c, 5f). Scattered lacZ expressing cells were present at 10 and 17 days following injury (FIG. 6c). To corroborate these findings with the TOPGAL transgenic mice and to demonstrate that cardiac fibroblasts were Wnt responsive, cardiac fibroblasts were isolated from hearts of wild type mice at 2, 5 and 10 days following injury and impressive up-regulation of Axin2 expression was observed in isolated cardiac fibroblasts (FIG. 5g), Axin2 being a marker of Wnt responsive cells (Gordon et al., *J. Biol. Chem.* 281:22429 (2006)). Phenotype of isolated cardiac fibroblasts was confirmed by demonstrating vimentin and DDR$^2$ expression (FIG. 6d). It is interesting to note that Wnt responsiveness of cardiac fibroblasts closely correlates with the temporal pattern of Wnt1 expression in cardiac fibroblasts following injury (FIG. 2i), suggesting that cardiac fibroblasts may be specifically responding to Wnt1. Taken together these observations demonstrate that the epicardium and fibroblasts in the injury region express Wnt1 and respond to Wnts suggesting a role of Wnt dependent regulation of these cardiac cell components in repair.

Figure 7:
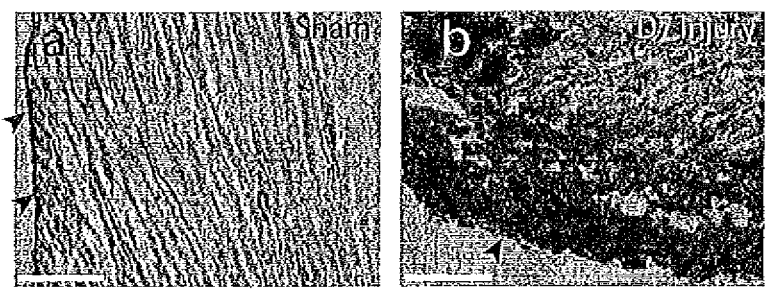
FIGS. 7a-7b show the epicardium expands following cardiac injury. Xgal staining of Wt-1Cre/R26R$^{lacZ}$ mice shows (a) sham injured heart (arrowheads show lac Z expressing epicardium); and (b) lacZ expressing epicardial cells at 7 days post injury (arrowhead shows expansion of epicardium). Scale bar: 100 µm.

To confirm epicardial cell expansion observed in TOPGAL transgenic mice after cardiac injury, acute cardiac injury was induced in 8 week old Wt-1Cre/R26R$^{lacZ}$ mice (Wilm et al., *Development* 132:5317 (2005)) and their hearts analyzed for lacZ expression. Wilms tumor 1 (Wt-1) is expressed in epicardial cells in the embryonic heart and labels the adult epicardium (Martinez-Estrada et al., *Nature Genet.* 42:89 (2010); Zhou et al., *Nature* 454:109 (2008)). Dramatic expansion of the epicardium was observed that peaked at 7 days (FIG. 7b) compared to sham injured animals (FIG. 7a). These findings support the notion that the epicardium dynamically activated by Wnt signaling rapidly expands after acute cardiac injury.

EXAMPLE 5

Wnt1 Activates a Pro-Fibrotic Response in Epicardium and Cardiac Fibroblasts The epicardium during cardiac development gives rise to cardiac fibroblasts by undergoing EMT and Wnts are known to regulate EMT in the developing heart. It was investigated whether the activated epicardium after cardiac injury recapitulates a developmental fate and is a source of activated fibroblasts. Tamoxifen inducible Collagen I Cre mice (Col1a2Cre(ER)T) were crossed with the lineage reporter R26R$^{lacZ}$ mice (Kapoor et al., *J. Clin. Invest.* 118:3279 (2008)), collagen 1 being an important component of cardiac scar and is expressed by cardiac fibroblasts (Sun et al., *Cardiovasc. Res.* 46:250 (2000)). Tamoxifen was administered for 10 days in Col1a2Cre(ER)T mice and stopped 5 days prior to injury. Sham injured animals received tamoxifen in an identical manner prior to sham injury. In another group of mice, tamoxifen injection was restarted on the day of injury and continued for 5 days. Hearts were harvested at 11 days following injury and analyzed for Xgal staining. Sham injured animals that received tamoxifen only prior to sham injury labeled rare cells in the epicardium and myocyte interstitium (FIG. 8a). Similarly, in animals that received tamoxifen only prior to injury, cells in the subepicardial region expressed lacZ (FIG. 8b) but only rare lacZ expressing cells were observed in the epicardium (FIG. 8b inset). However, animals that received tamoxifen both before and after injury had striking lacZ expression in the epicardium and subepicardial region (FIG. 8c). LacZ expression was seen in the epicardium even when adjacent myocytes appeared to be non-necrotic (FIG. 8d). The robust increase in lacZ expression in the epicardium of animals injected with tamoxifen both pre and post injury suggests that activated cardiac fibroblasts are generated in the epicardium and subepicardial regions after injury.

Figure 9:
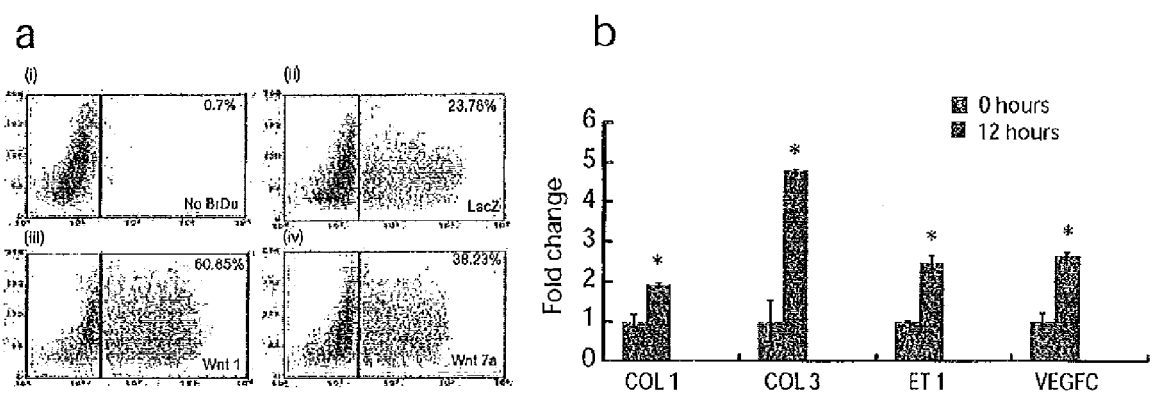
FIGS. 9a-9b show Wnt1 effects on cardiac fibroblasts in-vitro. (a) Wnt1 effects on cardiac fibroblast proliferation determined by BrdU uptake. Flow cytometry showing No BrdU control, and following over-expression of lacZ, Wnt1 or Wnt7a; (b) expression of pro-fibrotic genes (qPCR) following transient lentiviral infection of Wnt1 in cardiac fibroblasts (n=3, *p<0.05; mean±SEM).

The presence of activated fibroblasts in the epicardium is highly reminiscent of epicardial EMT during development, when the epicardial cells delaminate and undergo changes to adopt a mesenchymal phenotype. Epicardial cells were isolated from E12.5 dpf embryos; cells formed typical cobblestone epithelial colonies (FIG. 8e) and intensely stained with Wt-1 (FIG. 8g). Following treatment with TGFβ, a known inducer of EMT, cells at the periphery of the colony changed morphology into a more mesenchymal phenotype (FIG. 8f) and impressively down-regulated Wt-1 expression (FIG. 8h). Wt-1 is down-regulated following EMT in the developing embryo (Wilm et al., *Development* 132:5317 (2005); Carmona et al., *Cell Tissue Res.* 303:173 (2001); Moore et al., *Development* 126:1845 (1999)) and these observations are thus consistent with epicardial cells undergoing EMT. Next, the relationship of Wnt1 signaling and epicardial EMT was explored. Epicardial cells were treated with Wnt1 protein and dramatic down regulation of Wt-1 expression and several fold increased expression of genes associated with EMT such as MMPs (Kalluri et al., *J. Clin. Invest*, 119:1420 (2009); Thiery et al., *Cell* 139:871 (2009)) was observed (FIG. 8i). Wnt1 treatment also increased migration of epicardial cells in a scratch wound assay consistent with epicardial cells adopting a mesenchymal phenotype with enhanced migratory properties (FIGS. 8j, 8k). As cardiac fibroblasts in the region of injury expressed Wnt1 and were Wnt responsive as well, the effects of Wnt1 on cardiac fibroblast function were investigated. It was observed that Wnt1 over-expressing cardiac fibroblasts proliferate two-to-three times greater than lacZ expressing control cardiac fibroblasts (FIGS. 8l, 9a). In this respect, Wnt7A had a modest effect compared to that of Wnt1 (FIGS. 8l, 9a). Wnt1 treatment of cardiac fibroblasts also increased expression of genes known to promote cardiac fibrosis (FIG. 9b). These observations demonstrate that Wnt1 signaling promotes epicardial EMT, increases cardiac fibroblast activity and enhances a pro-fibrotic cardiac repair response.

EXAMPLE 6

Pro-Fibrotic Wnt Response is Critical for Cardiac Repair

Figure 10:
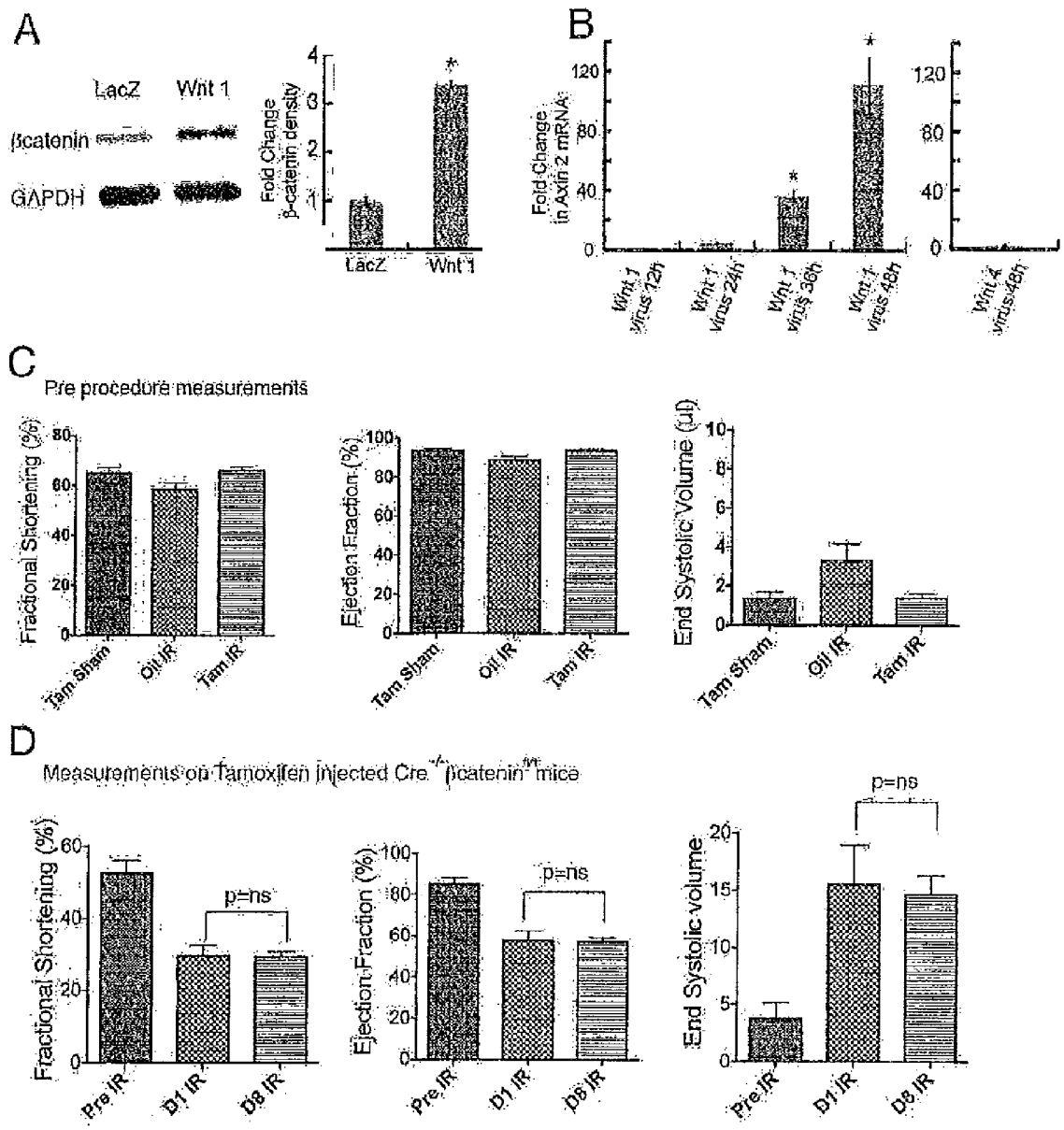
FIGS. 10a-10d show effects of Wnt1 on activating the canonical pathway (βcatenin) in cardiac fibroblasts and echocardiographic measurements prior to and following injury. (a) Western blotting and corresponding densitometric analysis of cytoplasmic βcatenin levels 48 hours following lentiviral infection of Wnt1 in cardiac fibroblasts. Cytoplasm was extracted using a FractionPREP Cell Fractionation Kit (Biovision, USA) and analyzed by anti-β-catenin (Cell Signalling Technology) and anti-GAPDH (Millipore). Densitometry of immunoreactive bands were analyzed with the UVP Gel Imaging System; (b) qPCR for Axin in cardiac fibroblasts at various time points following lentiviral infection of Wnt1 (left panel) or Wnt4 (right panel) (n=3, *p<0.05 compared to lacZ infected cardiac fibroblasts); (c) echocardiographic measurements of cardiac function and size performed prior to procedure (sham injury or ischemia-reperfusion injury). Tam sham: refers to mice (Col1a2CreER(T)/(β-catenin$^{fl/fl}$) which received tamoxifen but were subjected to sham procedure. Oil IR refers to similar groups that were subjected to ischemia-reperfusion injury but received oil instead of tamoxifen. Tam IR refers to groups (Col1a2CreER(T)/β-catenin$^{fl/fl}$) that received tamoxifen and were subjected to ischemia reperfusion injury; (d) echocardiographic measurements of Tamoxifen injected Cre$^{-/-}$/β-catenin$^{fl/fl}$ mice prior to and following ischemia reperfusion injury. Pre IR measurements were done just prior to induction of ischemia-reperfusion injury. D1 (Day 1) and D8 (Day 8) values correspond to measurements performed at 1 and 8 days following injury. (ns=non significant).
Figure 11:
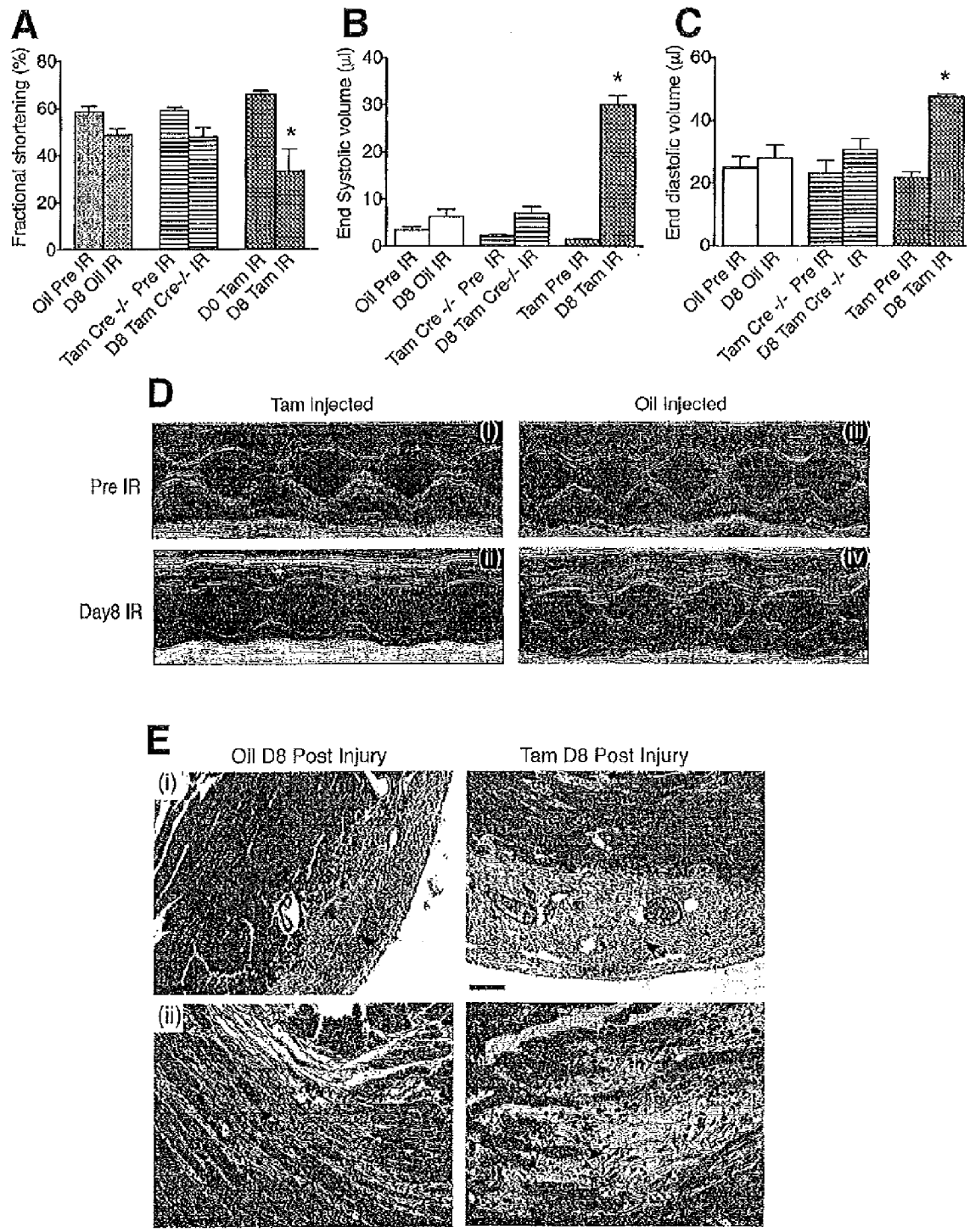
FIGS. 11a-11e show echocardiographic M Mode measurement of (a) fractional shortening; (b) end systolic volume; and (c) end diastolic volume (*p<0.05 of D8 Tam IR compared to D8 Oil IR and Tam Cre (-/-) mice IR; mean±SEM, n=15/group); (d) M mode echo of the cardiac chambers 8 days after injury in tamoxifen injected animals (Cre+/-) compared to oil injected ones; (e) Masson Trichrome staining of heart of Col1a2CreER(T)/bcatenin$^{fl/fl}$ animals 8 days following injury: (i) compact collagen deposition (arrow) in oil injected animal but loose granulation tissue and little collagen deposition in similar region of injury in tamoxifen injected animals (arrow); (ii) collagen deposition in subendocardial area of injury in oil injected animals (arrowhead) but disorganized granulation tissue with scant collagen deposition in similar regions in tamoxifen injected animals (arrowhead). Scale bar: 100 µm. (IR:ischemia-reperfusion; D8 refer to days following injury).

Using a loss of function approach, the effects of interrupting a pro-fibrotic Wnt response were investigated by abrogating downstream Wnt signaling in fibroblasts after cardiac injury. Dramatic up-regulation of β-catenin and activation of the canonical pathway in cardiac fibroblasts over-expressing Wnt1 were observed (FIGS. 10a, 10b). To interrupt downstream Wnt1 signaling specifically in cardiac fibroblasts, tamoxifen inducible Col1a2CreER(T)/βcatenin$^{fl/fl}$ mice were generated. Mice were administered tamoxifen for 10 days prior to injury (injections stopped 5 days prior to injury). Injections were restarted on the day of injury for 5 more days to target a pool of fibroblasts activated after injury. Col1a2CreER(T)/βcatenin$^{fl/fl}$ mice that received tamoxifen exhibited a dramatic phenotype with a 100% mortality by 12 days after injury. In contrast, 67% of the animals of same genotype (littermates) that were subjected to the same injury but received vehicle (oil) were alive at 14 days following injury (FIG. 10a). Induction of acute ischemia-reperfusion injury was associated with a peri-operative mortality (within a few hours) of 40% in the group with βcatenin deletion compared to 27% in the vehicle injected group. However survival in the tamoxifen injected group rapidly declined thereafter with only 26% survival by 4 days compared to 73% in the vehicle injected group. Echocardiographic analysis demonstrated gross left ventricular dilatation and decline in cardiac pumping function in tamoxifen injected mice that died within the first 4 days after injury (FIG. 11a). Animals that survived beyond the first 4 days had significant decrease in pumping function at 8 days compared to oil injected controls (FIGS. 11b, 11c) and exhibited a progressive dilatation in left ventricular size by 8 days of cardiac injury (FIG. 11d). Video recordings 8 days following injury demonstrated tamoxifen injected mice to have severely reduced activity compared to vehicle injected controls, consistent with symptomatic heart failure. There were no differences in cardiac parameters in any of the groups prior to the procedure (FIG. 10c). Similarly, tamoxifen injected animals that lacked Cre recombinase (Cre$^{-/-}$/βcatenin$^{fl/fl}$) and subjected to similar cardiac injury did not have progressive ventricular dilatation and no excess mortality was observed (FIG. 10d).

Histological analysis of hearts of animals with fibroblast specific βcatenin deletion demonstrated large transmural infarcts, with loose granulation tissue and dramatic reduction in collagen deposition in the injury region at 8 days compared to vehicle-injected controls (FIG. 11e). In hearts of tamoxifen injected animals that died within the first four days of injury (excluding peri-operative deaths), intramyocardial and sub-epicardial hemorrhages were observed. These observations reveal an unexpected but critical role of Wnt signaling in mediating a pro-fibrotic response that is essential for survival and prevention of cardiac dysfunction.

These experiments demonstrate a novel function of Wnt1 as a "cardiac response to injury" gene in driving early repair events in the heart. Wnt1 is expressed by epicardial cells and cardiac fibroblasts following acute cardiac injury. The epicardium is Wnt responsive, gets dynamically activated, expands and generates type 1 collagen expressing cardiac fibroblasts. Wnt1 enhances the pro-fibrotic function of cardiac fibroblasts and induces fibroblast proliferation as well as expression of pro-fibrotic genes. Interruption of downstream Wnt signaling in cardiac fibroblasts leads to a precipitous decline in cardiac function and organismal demise. Although the cause of such a rapid decline in cardiac function is not clear from these experiments, interruption of downstream Wnt signaling leads to severely decreased collagen deposition and loosely organized granulation tissue in the injured region. It is proposed that gross disorganization of wound healing along with little collagen deposition leads to an adverse rapid cardiac remodeling that results in acute ventricular dilatation and heart failure. Cardiac fibroblasts are known to generate tensile forces (Eastwood et al., *Proc. Inst. Mech. Eng. H* 212:85 (1998)) and consistent with Laplace's law, an interruption of cardiac fibroblast activation will lead to decreased tensile strength of the cardiac wall and predispose the cardiac chambers to dilate from the pressure of the blood within the chamber.

Figure 12:
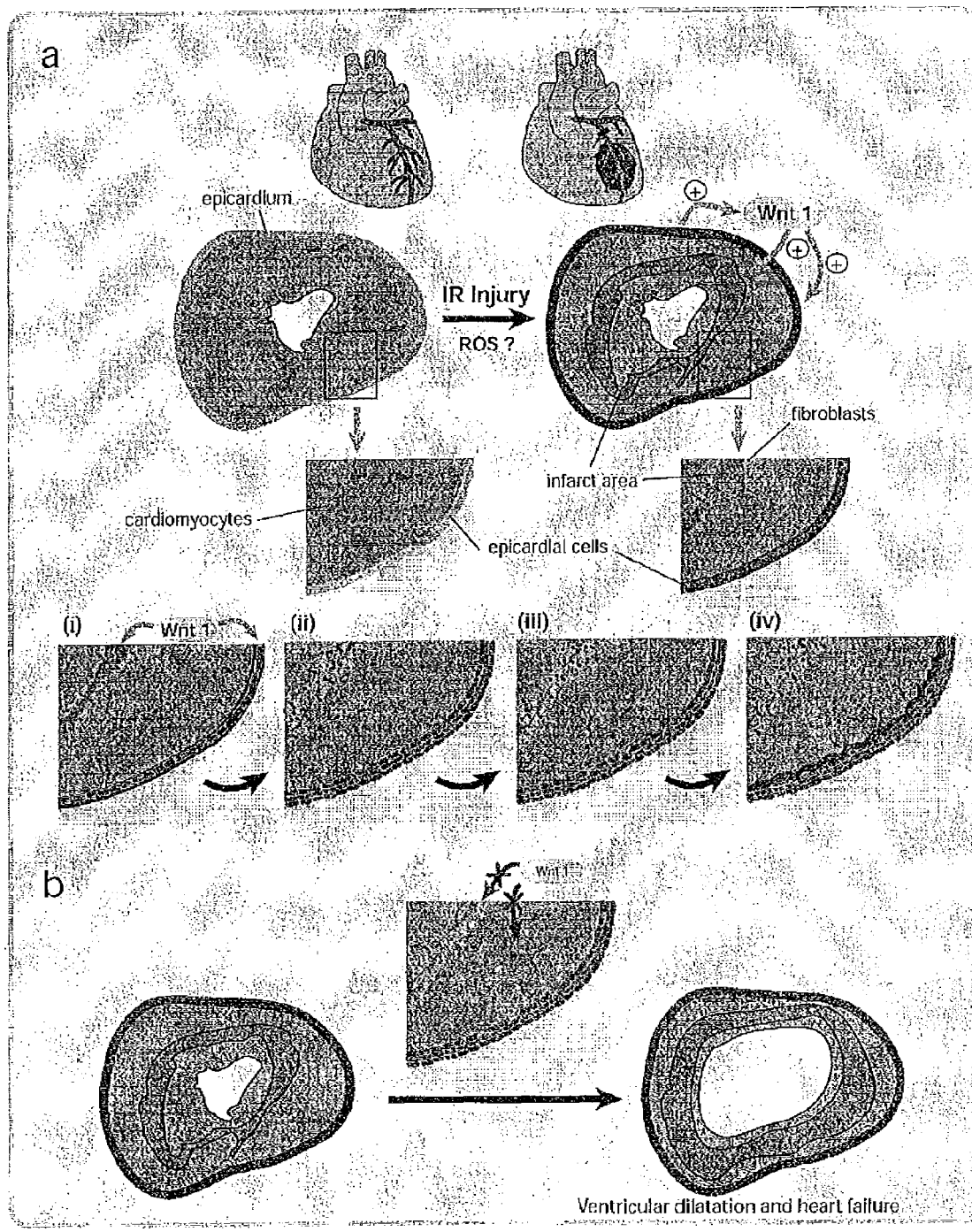
FIGS. 12a-12b show a Wnt dependent model of cardiac repair. (a) ischemia-reperfusion injury induces Wnt1 expression. Wnt1 activates (i) epicardial cells as well as cardiac fibroblasts in the region of injury; (ii) the epicardium expands; (iii) undergoes EMT to generate cardiac fibroblasts; cardiac fibroblasts in the region of injury continue to proliferate; (iv) fibroblasts in the epicardium lay down type 1 collagen in the subepicardial space; (b) interruption of this Wnt dependent pro-fibrotic repair response leads to rapid onset of acute cardiac dilatation and heart failure.

The epicardium is an epithelial layer surrounding the myocardium and is derived from the proepicardium during cardiac development (Manner et al., *Cells Tissues Organs* 169: 89 (2001)). The mammalian epicardium has been recently described to have mesenchymal and vascular progenitors and thymosin B4 identified as a molecule that activates and mobilizes epicardial progenitors and induces EMT (Smart et al., *Nature* 445:177 (2007); Limana et al., *J. Mol. Cell. Cardiol.* 48:609 (2010); Limana et al., *Circ. Res.* 101:1255 (2007); Bock-Marquette et al., *J. Mol. Cell. Cardiol.* 46:728 (2009)). These results reveal that the mammalian heart possesses an endogenous ability to activate its epicardium in a Wnt dependent manner after acute cardiac injury. The importance of epicardial EMT and subepicardial deposition of collagen following injury is underscored by the appearance of subepicardial hemorrhages in hearts of injured animals that had fibroblast specific interruption of downstream Wnt signaling. Based on these findings, a Wnt dependent model of mammalian cardiac repair is proposed involving a Wnt1 mediated pro-fibrotic response that activates cardiac fibroblasts and induces epicardial EMT to generate cardiac fibroblasts (FIGS. 12a-12b). Our model provides a plausible explanation to a long unanswered question of cardiac repair as to why fibroblast content increases even in regions remote from the region of cardiac injury (Camelliti et al., *Cardiovasc. Res.* 65:40 (2005); Weber, *J. Am. Coll. Cardiol.* 13:1637 (1989)). Organ wide activation of the epicardium and subsequent EMT to generate fibroblasts would result in them being present in regions remote from the area of injury. In lower animals such as zebrafish that possess the ability to regenerate, the epicardium is activated following injury, generates "blastema" and prepares a conducive environment for successful cardiac regeneration to occur (Lepilina et al., *Cell* 127:607 (2006)). These observations about epicardial activation bear a striking similarity to the response of the zebrafish heart after acute cardiac injury and suggest that the activation of the epicardium after cardiac injury is an evolutionary conserved response. However the outcome is fibrotic in contrast to a regenerative one in fish. Cardiac muscle regeneration in zebrafish takes weeks (Poss et al., *Science* 298:2188 (2002)) and higher pressures within the mammalian cardiac chambers might necessitate the mammalian heart to initially adopt a fibrotic repair response that is rapid and critical for survival, rather than a slower process of muscle regeneration. However such an initial pro-fibrotic injury response is critical as any interruption of this response leads to heart failure and death. One must live first to regenerate later.

EXAMPLE 7

Materials and Methods

Isolation of hEPC

Figure 17:
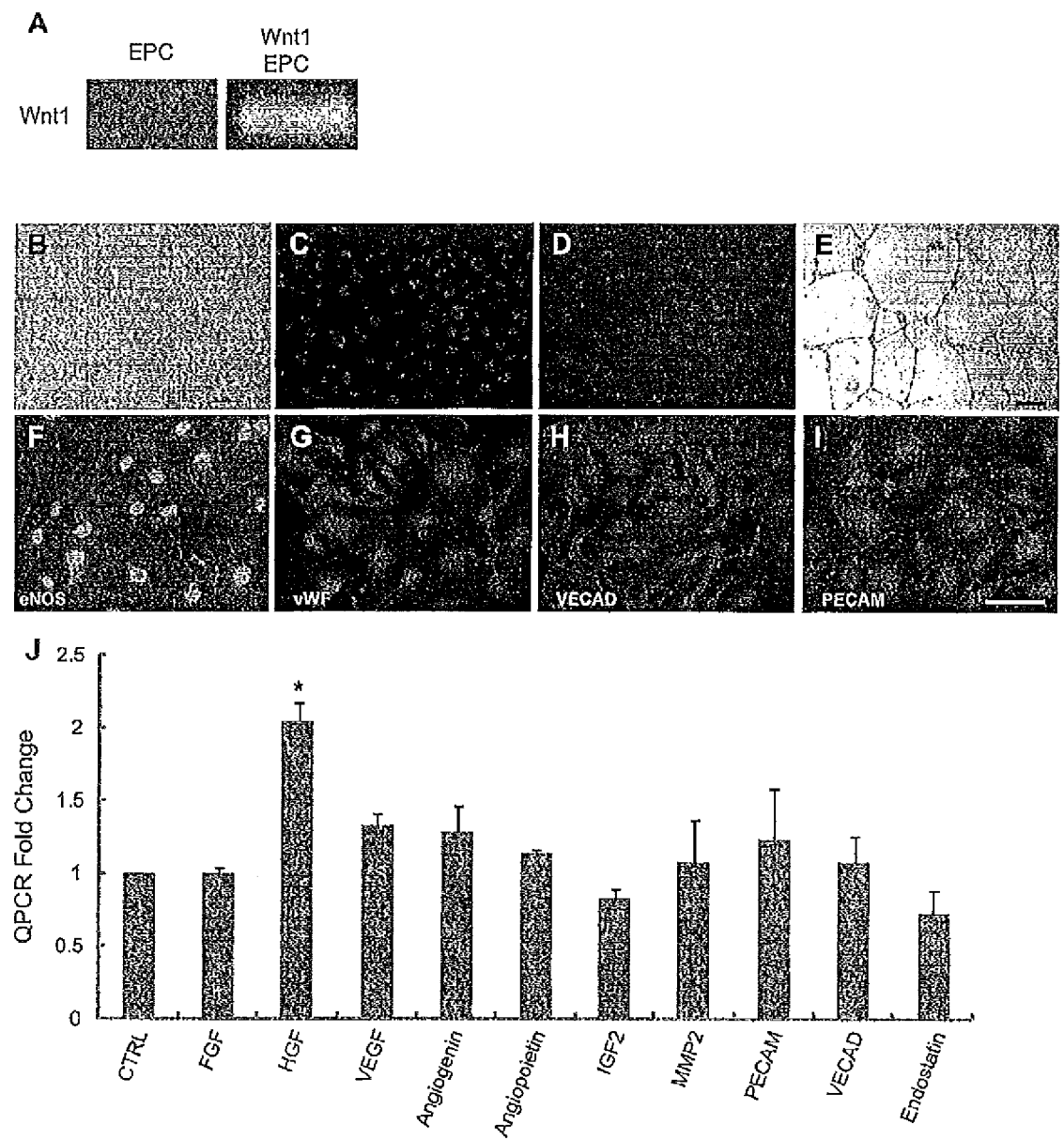
FIGS. 17a-17j. (a) PCR demonstrating that Wnt1 is not expressed in hEPCs, but only in hEPCs retrovirally infected with Wnt1 expressing vector; (b) typical cobblestone like colony of hEPCs that (c) uptakes both acetylated low-density lipoprotein and (d) Isolectin GS-IB$_4$, and forms (e) tubes on Matrigel. Human EPCs stain for common endothelial markers such as (f) eNOS, (g) vWF, (h) VECAD and (i) PECAM.

"Late outgrowth" hEPCs were isolated from peripheral blood of healthy subjects with prior approval from the Institutional Review Board of UNC Chapel Hill. Blood was mixed (1:2 ratio) with HBSS (0.5 mM EDTA and 0.1% BSA) and mononuclear cells were isolated by density gradient centrifugation using Ficoll Paque (15 mL Ficoll to 35 mL blood, 400 g for 30 min at room temperature (RT)). The mononuclear layer was collected and washed twice with EGM-2 (Lonza) media (10% FBS) (350 g, 15 min at RT). Cells were then plated on 6 well plates (precoated with collagen type 1) (20× $10^6$ cells/well) in EGM-2 media (10% FBS) and incubated at 37° C. and 5% $CO_2$. Media was initially replaced after 72 h, then every other day. Cobblestone "late outgrowth" EPC colonies were observed within 2-3 weeks. EPCs exhibited dual uptake of acetylated low-density lipoprotein (Alexa 594 DilAcLDL, Invitrogen) and Isolectin GS-1$B_4$ from *Griffonia simplicifolia* (Alexa 488 labeled, Invitrogen) (FIG. 17b). Cells were first incubated with Dil-acLDL (10 µg/mL) for 4 h, washed with media, and then incubated with isolectin (2.5 µg/mL) for 1 h. EPCs were further characterized by immunofluorescence staining: eNOS (anti-eNOS, SD Biosciences), vWF (anti-vWF, Santa Cruz), VECAD (anti-VeCadherin, Abeam) and PECAM (anti-PECAM, Santa Cruz) (FIGS. 18e-18h). Cells were stained using the primary antibody at 1:40 dilution for 1 h at RT, followed by the use of appropriate secondary at a dilution of 1:2000 for 1 h at RT. Controls were established by excluding the primary antibody.

Proliferation hEPCs ($5 \times 10^3$) were plated in 48-well plates in EGM-2 media (10% FBS) and were allowed to attach overnight, EPCs were then serum starved for 8 h in EGM-2. Cells were then supplemented with EGM-2 (2% FBS), EGM-2 (2% FBS) and Wnt1 protein (AbD Serotec) at 5 or 25 nM or EGM-2 (10% FBS) as a positive control. Proliferation was assayed at 72 h using the CyQUANT cellular proliferation assay kit (Invitrogen).

Angiogenesis

EPCs ($3.5 \times 10^4$) were plated on Matrigel™ (SD Biosciences) coated wells in 24-well plates in appropriate media. For canonical pathway inhibition, human DKK-1 protein (R&D Systems) was added at a concentration of 50 nM at the same time with Wnt1. All the tubes formed in each well were counted at 24 h. For the siRNA inhibition experiments, 50 nM scrambled siRNA or anti-HGF (sc-37111, Santa Cruz Biotechnology, Inc) or anti-FZD4 siRNA (Abnova, H00008392) were added at the same time with the Wnt1 protein and tube analysis was performed after 24 hours by counting the total number of tubes in each well.

Q-PCR

Total RNA was extracted using the SV total RNA isolation system (Promega) and cDNA was synthesized using the Reverse Transcription System (Promega). Q PCR reactions were performed on a BioRad IQ5 Detection System.

Immunohistochemistry

Immunohistochemistry experiments were carried out using anti-Wnt1 (ABR) and anti-PECAM (Santa Cruz) (1:200, 1 h at RT), followed by antibodies and reagents from Vectastain Kit (Vector Laboratories). Staining of sections of human angiosarcomas was approved by the IRB of the University of North Carolina, Chapel Hill.

Retroviral Infection

Retroviruses were generated using pRetroX-IRES-Zs-Green1 plasmid (Clontech) with or without the Wnt1 gene at the viral core facility at UNC-Chapel Hill. hEPCs were infected at an MOI 1:10. Infected hEPCs were sorted to >95% purity using iCyt Reflection sorter (FIG. 18b).

Western Blot Analysis hEPC were lysed and cytosolic protein was isolated using BioVision Cell Fractionation System (K25-50). Rabbit anti-β-catenin antibody (1:1000) (Cell Signaling, 5692) was used, followed by an appropriate secondary (1:1000).

Animal Models of Hind Limb Ischemia

All animal experiments were approved by the Institutional Animal Care and Use Committee of UNC Chapel Hill. For Wnt1 protein model, 6-week old C57 background mice (Jackson laboratory) were used and for hEPC injection experiments, 6-week old immunocompromised mice (Jackson Laboratories, 005557) were used. Mice were anesthetized with 2% isofluorane and subjected to unilateral hindlimb ischemia. The femoral artery was ligated and excised immediately distal to the bifurcation of the anterior epigastric and lateral caudal femoral arteries. The anterior epigastric artery was also ligated. Blood flow measurements were done using a computer-assisted Laser Doppler perfusion image analyzer (Periscan PIM 3, Perimed) pre- and post-operatively, and at day 1, 3, and 7, maintaining body temperature at 37.0±0.5° C. Injection of PBS, Wnt1, or EPCs ($5 \times 10^5$) (100 µL) were performed at 15 min following surgery, in the gastrocnemius muscle. At 7 days, gastrocnemius muscles were isolated, fixed in 4% PFA for 30 min and 30% sucrose overnight, embedded in OCT compound and flash frozen in liquid nitrogen. Muscle capillary densities of were analyzed by counterstaining with isolectin. Capillary density was determined by counting capillary vessels in 10 randomly selected microscopic fields.

Statistical Analysis

All statistical correlations were calculated as standard t-test. Results expressed in mean±SEM.

EXAMPLE 8

Figure 13:
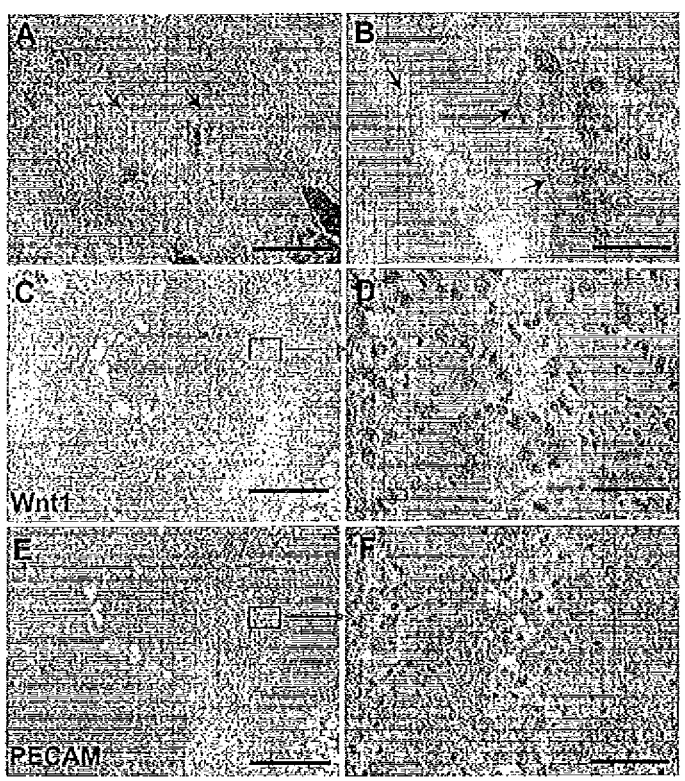
FIGS. 13a-13f show Wnt1 is expressed in developing endothelium and reactivated in human skin angiosarcomas. (a) Xgal staining (black arrow) of the AGM region in E10.5 dpf embryos (gray arrow points to dorsal aorta); (b) higher magnification of the dorsal aorta demonstrates Xgal staining of endothelial cells (black arrows) and of cells of hematopoietic origin (gray arrow). Sections were counterstained with nuclear fast red; (c-f) immunohistochemistry for Wnt1 and PECAM in adjacent sections (7 µm apart) of human skin angiosarcoma demonstrates colocalization of Wnt1 and PECAM in highly undifferentiated regions; (a, bar: 200 µm); (b, bar 40 µm); (c, e, bar: 500 µm); (d, f: bar: 40 µm).

Wnt1 is Expressed in the Developing Vasculature and Reactivated in Vascular Tumors in Adult Life It was observed that Wnt1 was expressed in a subset of endothelial cells lining the dorsal aorta as well as in endothelial rich regions of malignant human angiosarcomas. The aorta-gonado-mesonephric region (AGM) (FIG. 13a) of E10.5 dpf Wnt1Cre/R26R$^{lacZ}$ embryos was examined, and strong lacZ expression was observed in a subset of endothelial cells lining the dorsal aorta (FIG. 13b). LacZ expression was also seen in the subendothelial region as well as in presumably hematopoietic cells residing in the lumen of the aorta (FIG. 13b). Although a portion of the aortic arch is derived from Wnt1 expressing neural crest cells, hEPCs do not express Wnt1 (FIG. 17a), suggesting that Wnt1 expressing endothelial cells observed in the dorsal aorta either migrate, die or remain below the detection threshold of our assay. It was also noted that Wnt1 is re-expressed in malignant human angiosarcomas. Human skin angiosarcomas were examined and it was observed that highly undifferentiated regions of the tumor stained for Wnt1. Regions of the tumor richly staining for Wnt1 (FIGS. 13c, 13d) also stained for endothelial markers such as PECAM (FIGS. 13e, 13f). The above data demonstrate that Wnt1 is expressed in developing endothelial cells during embryonic vasculogenesis as well as is dramatically reactivated in endothelial rich angiosarcomas. These observations led to an investigation whether Wnt1 exerts angiogenic effects on post natal human endothelial progenitors and whether this molecule could be therapeutically deployed to enhance blood flow in ischemic tissues.

EXAMPLE 9

Figure 14:
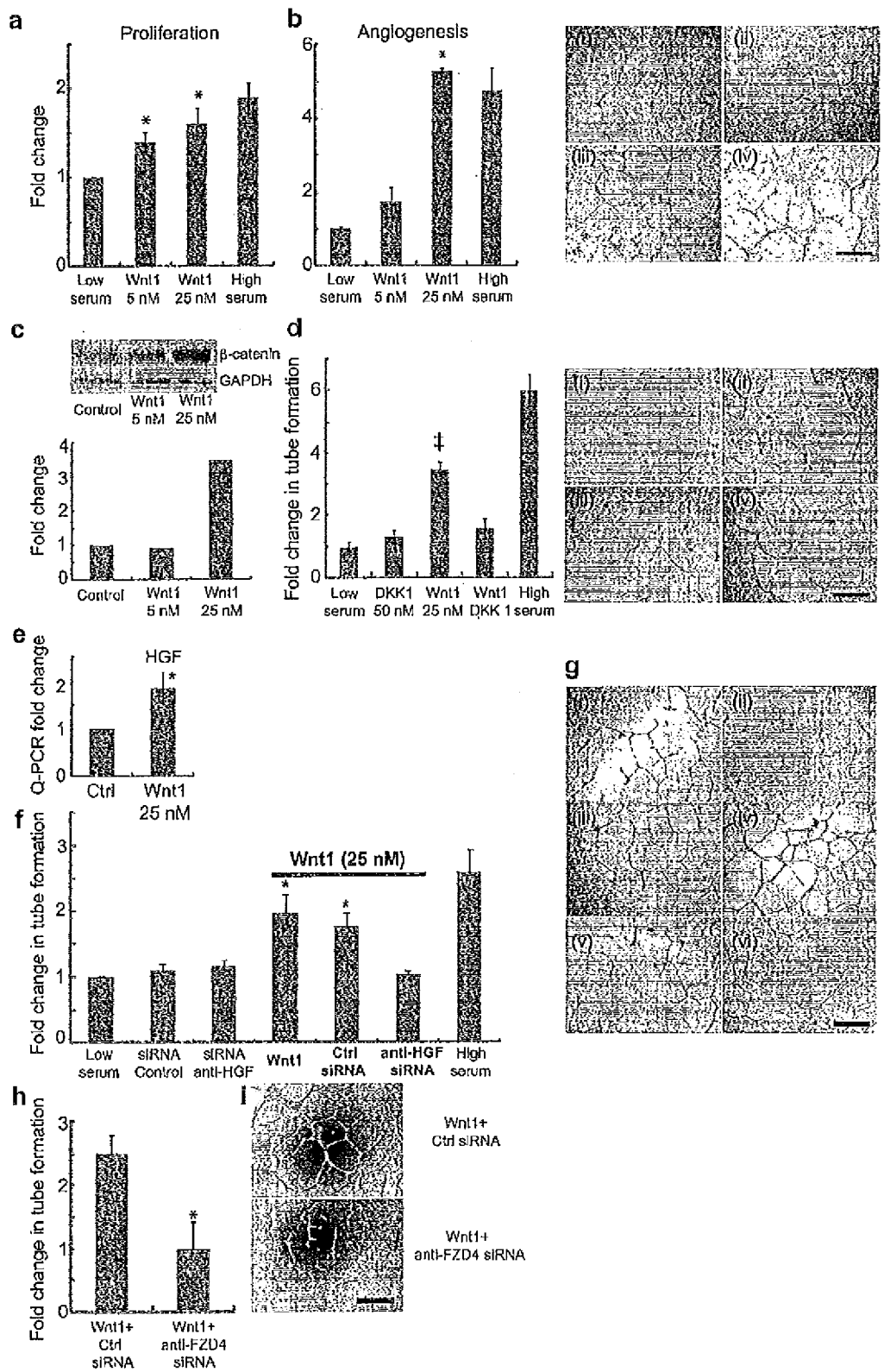
FIGS. 14a-14i show Wnt1 effects on hEPC and downstream regulators. (a) Wnt1 stimulates hEPC proliferation in a concentration dependent manner (n=5, (*p<0.05) between Wnt1 at 5 or 25 nM vs. low serum); (b) Wnt1 stimulates in vitro angiogenesis of hEPCs assayed by Matrigel tube formation. Human EPCs were plated at a density of 3.4×10$^4$ cells/well in a 24 well plate and at 24 h following Wnt1 addition, total number of closed tubes were counted in the entire well; (n=3, (*p<0.05) between Wnt1 at 25 nM vs. low serum); (i) low serum (2%) control; (ii) Wnt1 at 5 nM; (iii) Wnt1 at 25 nM and (iv) 10% serum positive control; (c). Western blot for β-catenin on Wnt1 treated hEPC shows a concentration dependent increase in cytoplasmic catenin with corresponding densitometry analysis; (d) canonical inhibitor DKK1 (50 nM) antagonizes Wnt1 effects on Matrigel tube formation (n=3, (t pc 0.05) between Wnt1 at 25 nM vs. DKK1 and Wnt1); (i) low serum control; (ii) Wnt1 at 25 nM; (iii) Wnt1 at 25 nM and DKK-1 at 50 nM; (iv) 10% serum positive control; (e) qPCR shows a 2 fold increase of HGF expression in hEPC following Wnt1 treatment; (n=3, *p<o 05); (f) inhibition of Wnt1-mediated tube formation via siRNA against HGF; (g) (i) control scrambled siRNA and (ii) siRNA against HGF alone did not have an effect on tube formation when compared to low serum control; (iii) Wnt1 alone enhances tube formation and (iv) Wnt1 effects are maintained when scrambled siRNA is present; (v) HGF siRNA inhibits Wnt1 tube formation by 50%; (vi) tube formation with 10% serum control (n=5, (*p<0.05) between Wnt1, or (Wnt1+scrambled siRNA) vs. (Wnt1+antiHGF siRNA); (bars: 500 pm); (h,i) inhibition of Wnt1-mediated tube formation via siRNA against FZD4 (n=3, *p<005).

Wnt1 Effect on Endothelial Progenitor Cells hEPCs were isolated from peripheral blood of healthy subjects and their endothelial phenotype confirmed (FIGS. 17b-17i). The effects of Wnt1 protein on proliferation and angiogenesis were investigated by treating hEPCs with human recombinant Wnt1 protein under low serum conditions. It was observed that Wnt1 protein significantly enhanced EPC proliferation (FIG. 14a) in a concentration dependent manner and dramatically induced tube formation of hEPC within 24 hours compared to untreated controls (FIG. 14b). The downstream mechanisms of pro-angiogenic effects of Wnt1 on hEPC were subsequently investigated. Several recent studies have demonstrated the importance of non-canonical Wnt pathways in modulating angiogenesis (Cheng et al., *Biochem. Biophys. Res. Commun.* 365:285 (2008)) as well as the ability of Wnt1 to exert its effects through β-catenin independent pathways (You et al., *Cancer Res.* 64:3474 (2004); Ziemer et al., *Mol. Cell. Biol.* 21:562 (2001)). In the canonical Wnt pathway, Wnt binds to the frizzled receptor in association with LRP5/6 and leads to GSK3b inhibition and accumulation of β-catenin, that enters the nucleus and interacts with TCF/LEF transcription factors to initiate target gene transcription (Gordon et al., *J. Biol. Chem.* 281:22429 (2006)). Dickoppf (DKK1) specifically inhibits the canonical Wnt pathway but leaves the non-canonical pathway intact (Gordon et al., *J. Biol. Chem.* 281: 22429 (2006)). It was interrogated whether Wnt1 exerts its salutary effects on hEPC via the canonical β-catenin pathway. Human EPCs were grown under low serum conditions with or without Wnt1 for 24 hours followed by analysis of cytoplasmic β-catenin levels. Western blot analysis showed a concentration dependent increase in cytoplasmic β-catenin levels in hEPCs treated with Wnt1 (FIG. 14c). Next, the canonical pathway was inhibited using DKK1 to determine the effects of this pathway in mediating Wnt1 pro-angiogenic effects. Human EPCs seeded onto Matrigel coated plates were treated with Wnt1 for 24 hours in the presence or absence of DKK1. The addition of Wnt1 increased tube formation by almost 4 fold and the concomitant addition of DKK1 reduced tube formation by almost 50%. These studies thus demonstrate that Wnt1 exerts pro-angiogenic effects on hEPC via the canonical β-catenin pathway. To explore whether Wnt1 might exert pro-angiogenic effects via upregulation of angiogenic cytokines, changes in expression of several angiogenic molecules were screened for following Wnt1 treatment of hEPC, (FIG. 17j) and a significant increase in hepatocyte growth factor (HGF) expression was demonstrated (FIG. 14e). In fact enhanced Wnt signaling is associated with increased HGF activity in epithelial cells and colon tumors (Vermeulen et al., *Nature Cell Biol.* 12:468 (2010); Papkoff et al., *Biochem. Biophys. Res. Commun.* 247:851 (1998)). Next, the effects of Wnt1 on hEPC tube formation were determined following silencing of HGF with RNAi (FIG. 18a) and a 50% decrease in tube formation was observed, suggesting a critical role of HGF in Wnt1 mediated angiogenesis (FIGS. 14f, 14g). Wnts are known to initiate signal transduction after binding to transmembrane Frizzled receptors. Ten different types of Frizzled receptors have been identified so far (Cadigan et al., *Genes Dev,* 11:3286 (1997)) and a preliminary PCR screen revealed expression of Fzd4 and Fzd6 both in hEPCs and HUVECs. Fzd4 is known to play a crucial role in retinal vascularization (Ye et al., *Cell* 139:285 (2009)). Next, Fzd4 expression was inhibited with siRNA and it was observed that Wnt1 treated hEPC transfected with Fzd4 siRNA formed approximately half the number of tubes on Matrigel compared to hEPCs transfected with a scrambled siRNA control (FIGS. 14h, 14i).

EXAMPLE 10

Wnt1 Increases Angiogenesis and Blood Flow to Ischemic Limbs

Figure 15:
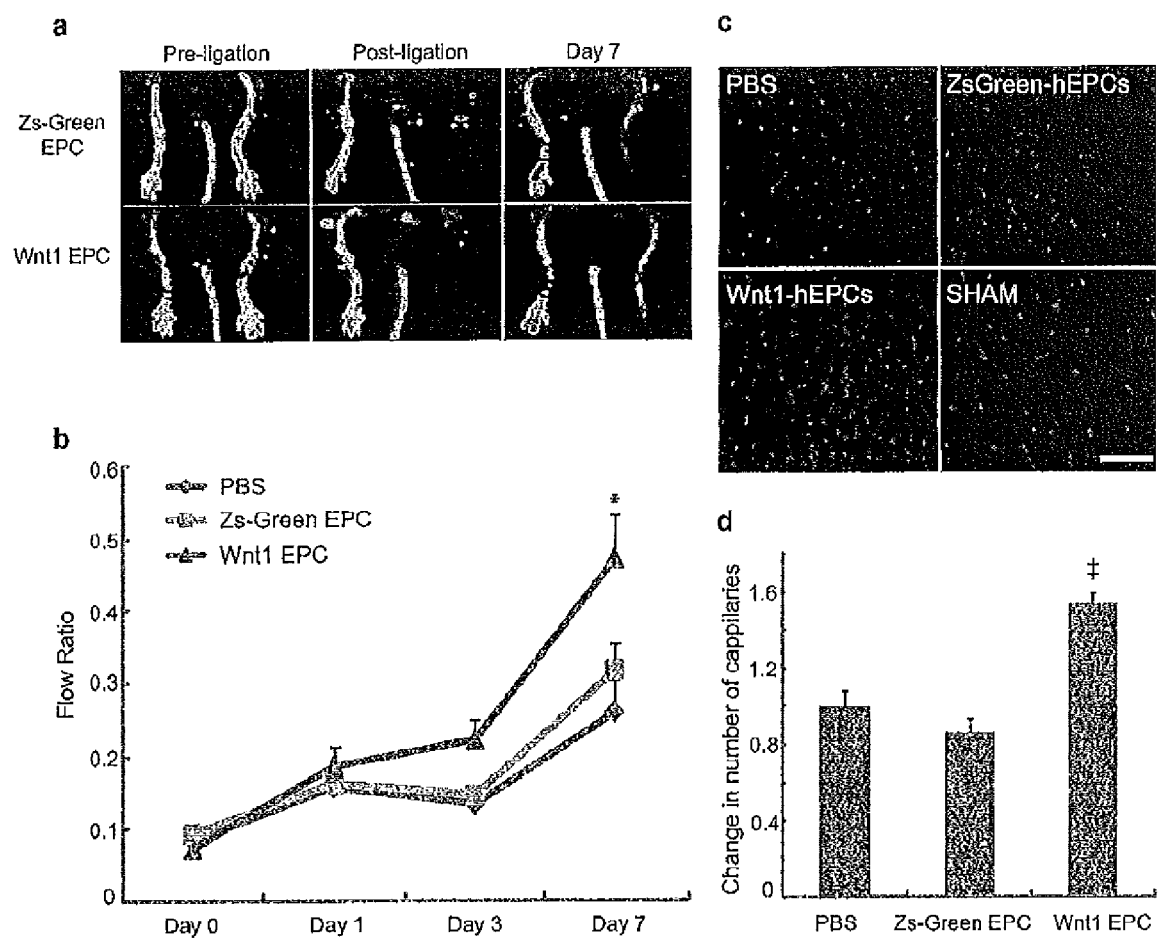
FIGS. 15a-15d show Wnt1 overexpressing hEPCs enhance blood flow recovery in ischemic limb. (a) Doppler analysis of NOD/SCID mice pre-ischemia, post-ischemia and at 7 days following injection of Wnt1 hEPC or Zs-Green hEPC; (b) time course of blood flow recovery for PBS injected mice (diamonds), (n=7), hEPC overexpressing ZsGreen (squares), (n=12) and EPC overexpressing ZsGreen and Wnt1 (triangles), (n=12). Statistical significance (*p<0.05) was obtained between the EPC overexpressing Wnt1 and the control groups. There was no statistical difference in blood flow in the injured limb between animals which received PBS or ZsGreen-hEPC; (c) representative capillary staining for PBS, ZsGreen-hEPCs, Wnt1-hEPC injected mice as well as sham injured muscle (bar: 100 µm). Capillaries were identified by staining sections with isolectin GS-IB$_4$; (d) Capillary count analysis on 4 mice per group, (Statistical significance (p<0.05) was obtained between the Wnt1-hEPC injected mice and the control groups).

Having demonstrated that Wnt1 enhances hEPC function in vitro, it was next investigated whether administration of Wnt1 over-expressing hEPC in NOD/SCID immunodeficient mice (Agliano et al., *Int. J. Cancer* 123:2222 (2008)) increases angiogenesis and improves blood flow to ischemic hind limbs. hEPC were infected with retroviruses containing Wnt1 co-expressing ZsGreen fluorescent protein (Wnt1-hEPC) or control vector carrying ZsGreen alone (ZsGreen-hEPC). Cells were then sorted for ZsGreen using flow cytometry to obtain a purity of >95% (FIG. 18b). Unilateral hind limb ischemia was induced via femoral artery ligation and excision. Immediately after surgery, the blood flow in both limbs was evaluated using Laser Doppler scanning (FIG. 15a) to ensure successful distal interruption of blood flow. PBS, Zs-Green-hEPC or Wnt1-hEPC (5×10$^5$ cells) were then injected directly into the gastrocnemius muscle. The recovery of blood flow in the pedal area was quantified at 1, 3, and 7 days and expressed as the ratio of blood flow between the ischemic and uninjured limb. Mice were euthanized 7 days following induction of hind limb ischemia and the gastrocnemius muscle analyzed for capillary formation. Injection of Wnt1-hEPCs resulted in an almost two fold significant increase in blood flow at 7 days following injury compared to injection of hEPCs that express ZsGreen alone (FIGS. 15a, 15b). Staining for capillaries with isolectin showed a two-fold increase in capillary formation in ischemic muscle (FIGS. 15c, 15d). When it was examined whether injected hEPC incorporated into new capillaries in ischemic tissues, no differences were observed in the number of ZsGreen-hEPC and Wnt1-hEPC injected cells that also stained with isolectin (FIG. 18c). These observations demonstrate that the mechanism of benefit is not directly related to hEPC incorporating into new blood vessels and suggests a paracrine effect on native endothelial cells or endothelial progenitor cells.

Figure 16:
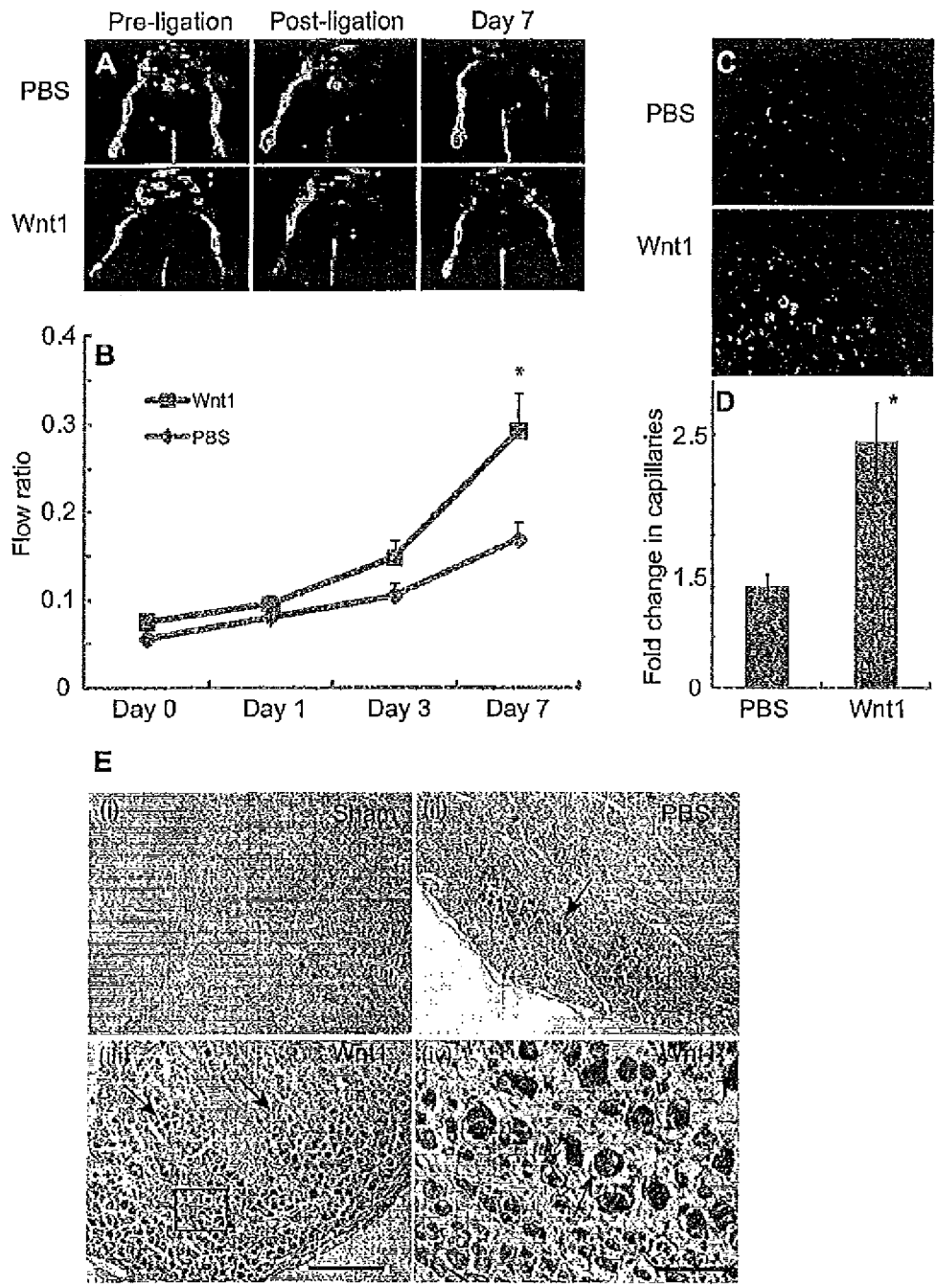
FIGS. 16a-16e show Wnt1 protein enhances blood flow recovery in ischemic limb. (a) Doppler analysis of C57B116 mice pre-ischemia, immediately post artery ligation and at 7 days following injury in PBS and Wnt1 injected animals; (b) flow recovery as a function of time in PBS (diamonds, n=8) and Wnt1 (squares, n=12) groups shows a significant 2 fold increase in blood flow at 7 days in Wnt1 injected mice (*p<0.05); (c) capillary count by isolectin staining of PBS and Wnt1 injected animals. Capillaries were identified by staining sections with isolectin GS-IB$_4$ and the total number of capillaries in 10 random high power fields was counted; (d) fold change in number of capillaries of Wnt1 injected animals vs. PBS group; (e) immunohistochemistry for HGF shows (i) no staining for HGF in sham injured muscle; (ii) focal staining in PBS injected injured muscle (black arrow); (iii) diffuse expression of HGH in injured muscle injected with Wnt1 (black arrows); (iv) higher magnification of same (bar: 500 µm, Wnt1 high magnification, bar: 100 µm).

It was subsequently determined whether injection of Wnt1 protein alone can increase blood flow in ischemic limbs. Following induction and confirmation of hind limb ischemia by laser Doppler scanning (FIG. 16a), Wnt1 protein (1 µg/animal) or PBS was injected directly in the gastrocnemius muscle. By 7 days, Wnt1 injected mice had a significantly higher blood flow compared to PBS controls (FIGS. 16a, 16b). The two-fold increase in the blood flow recovery was associated with a higher number of capillaries in Wnt1 injected hindlimbs (FIGS. 16e, 16d). As Wnt1 effects on hEPC were mediated by HGF, it was determined whether HGF was increased in Wnt1 injected ischemic hindlimbs compared to PBS injected controls. Analysis of hind limb sections injected with PBS following injury, demonstrated focal upregulation of HGF in the region of injury (FIGS. 16e(i), 16e(ii)) consistent with prior reports of ischemia inducing HGF expression (Ono et al., *Circulation* 95:2471 (1997)). However, animals that received Wnt1 in ischemic tissues showed dramatic expression of HGF (FIG. 16e(iii)). HGF was mainly expressed by muscle fibers (FIG. 16e(iv)) in the region of injury. These observations support the in vitro data of the critical roles of HGF in mediating Wnt1 effects on angiogenesis:

In summary, a novel function of Wnt1 as a pro-angiogenic molecule was demonstrated. Wnt1 acting through Fzd4 receptor enhances function of hEPCs and increases blood flow to ischemic extremities by a paracrine effect mediated by HGF. Our observations form a rational underpinning for the use of Wnt1 as a therapeutic protein for enhancing hEPC function and increasing blood flow to ischemic extremities.

The foregoing is illustrative of the present invention, and is not to be construed as limiting thereof. The invention is defined by the following claims, with equivalents of the claims to be included therein.

That which is claimed is:

1. A method of activating the epicardium in the ischemic heart of a subject, comprising delivering recombinant Wnt1 to the subject.

2. The method of claim 1, wherein the Wnt1 is delivered directly to the heart of the subject.

3. The method of claim 1, wherein delivering Wnt1 comprises delivering a Wnt1 polypeptide.

4. The method of claim 1, wherein delivering Wnt1 comprises delivering a polynucleotide encoding a Wnt1 polypeptide.

5. The method of claim 1, wherein delivering Wnt1 comprises delivering a cell expressing a Wnt1 polypeptide.

6. The method of claim 5, wherein the cell is modified to recombinantly express Wnt1.

7. The method of claim 1, wherein the subject is a human.

* * * * *